United States Patent
Pool

(10) Patent No.: US 12,290,290 B2
(45) Date of Patent: May 6, 2025

(54) SYSTEM AND METHOD FOR ALTERING ROTATIONAL ALIGNMENT OF BONE SECTIONS

(71) Applicant: NuVasive Specialized Orthopedics, Inc., San Diego, CA (US)

(72) Inventor: Scott Pool, Laguna Hills, CA (US)

(73) Assignee: NuVasive, Inc., San Diego, CA (US)

( * ) Notice: Subject to any disclaimer, the term of this patent is extended or adjusted under 35 U.S.C. 154(b) by 385 days.

(21) Appl. No.: 17/810,469

(22) Filed: Jul. 1, 2022

(65) Prior Publication Data

US 2022/0346846 A1 Nov. 3, 2022
US 2023/0233236 A9 Jul. 27, 2023

Related U.S. Application Data

(63) Continuation of application No. 16/841,925, filed on Apr. 7, 2020, now Pat. No. 11,406,432, which is a
(Continued)

(51) Int. Cl.
*A61B 17/72* (2006.01)
*A61B 17/17* (2006.01)
(Continued)

(52) U.S. Cl.
CPC ...... *A61B 17/7216* (2013.01); *A61B 17/1725* (2013.01); *A61B 17/68* (2013.01);
(Continued)

(58) Field of Classification Search
CPC ....... A61B 17/68; A61B 17/025; A61B 17/72; A61B 17/7216; A61B 2017/681
(Continued)

(56) References Cited

U.S. PATENT DOCUMENTS 2,702,031 A 2/1955 Leslie
3,111,945 A 11/1963 Von Solbrig
(Continued)

FOREIGN PATENT DOCUMENTS

CN 1697630 A 11/2005
CN 101040807 A 9/2007
(Continued)

OTHER PUBLICATIONS

International Search Report for PCT/US2010/047842, ISA, mailed Nov. 4, 2010, pp. 4.
(Continued)

*Primary Examiner* — Ellen C Hammond
*Assistant Examiner* — Christina Negrellirodriguez

(57) ABSTRACT

The disclosure describes systems and methods for altering bone sections in a patient. In one embodiment, a system may include an intramedullary implant including: a housing configured to be secured to a first section of bone, where the housing may include one or more shaft engaging grooves axially extending along an inner surface thereof; a distraction shaft configured to be secured to a second section of bone, where the distraction shaft may include one or more grooves axially extending along an inner surface thereof. The system may further include an actuator disposed within the housing and operably coupled to the distraction shaft, and in response to rotation of the actuator, the one or more grooves of the distraction shaft may engage with the one or more shaft engaging grooves of the housing, causing axial displacement of the distraction shaft relative to the housing.

18 Claims, 25 Drawing Sheets

Related U.S. Application Data continuation of application No. 15/989,672, filed on May 25, 2018, now Pat. No. 10,646,262, which is a continuation of application No. 15/207,763, filed on Jul. 12, 2016, now Pat. No. 10,105,167, which is a continuation of application No. 14/146,336, filed on Jan. 2, 2014, now Pat. No. 9,393,117, which is a continuation of application No. 13/370,966, filed on Feb. 10, 2012, now Pat. No. 8,715,282.

(60) Provisional application No. 61/472,055, filed on Apr. 5, 2011, provisional application No. 61/442,658, filed on Feb. 14, 2011.

(51) Int. Cl.

| | | |
|---|---|---|
| *A61B 17/68* | (2006.01) | |
| *A61B 17/92* | (2006.01) | |
| *A61B 50/30* | (2016.01) | |
| *A61B 50/34* | (2016.01) | |
| *A61F 2/28* | (2006.01) | |
| *A61B 17/00* | (2006.01) | |
| *A61B 50/33* | (2016.01) | |

(52) U.S. Cl.
CPC ............ *A61B 17/921* (2013.01); *A61B 50/30* (2016.02); *A61B 50/34* (2016.02); *A61F 2/28* (2013.01); *A61B 2017/00411* (2013.01); *A61B 2017/00845* (2013.01); *A61B 2017/681* (2013.01); *A61B 50/33* (2016.02)

(58) Field of Classification Search
USPC .......................................................... 606/62
See application file for complete search history.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,810,259 A | 5/1974 | Summers |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Parsley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |

(56) References Cited

U.S. PATENT DOCUMENTS

| | | |
|---|---|---|
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Bubler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,601,156 B2 | 10/2009 | Robinson |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,887,566 B2 | 2/2011 | Hynes |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,472 B2 | 11/2011 | Walker et al. |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,105,363 B2 | 1/2012 | Fielding et al. |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,517 B2 | 4/2012 | Trieu et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |

(56) References Cited

U.S. PATENT DOCUMENTS

| | | |
|---|---|---|
| 8,282,671 B2 | 10/2012 | Connor |
| 8,298,240 B2 | 10/2012 | Giger et al. |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,419,801 B2 | 4/2013 | Disilvestro et al. |
| 8,425,608 B2 | 4/2013 | Dewey et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,715,282 B2 | 5/2014 | Pool |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,852,187 B2 | 10/2014 | Pool et al. |
| 8,870,881 B2 | 10/2014 | Rezach et al. |
| 8,870,959 B2 | 10/2014 | Arnin |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,393,117 B2 | 7/2016 | Pool |
| 10,105,167 B2 | 10/2018 | Pool |
| 10,646,262 B2 | 5/2020 | Pool |
| 2001/0034524 A1 | 10/2001 | Bales |
| 2002/0050112 A1 | 5/2002 | Koch et al. |
| 2002/0072758 A1 | 6/2002 | Reo et al. |
| 2002/0111629 A1 | 8/2002 | Phillips |
| 2002/0143344 A1 | 10/2002 | Taylor |
| 2002/0151898 A1 | 10/2002 | Sohngen et al. |
| 2002/0151978 A1 | 10/2002 | Zacouto et al. |
| 2002/0164905 A1 | 11/2002 | Bryant |
| 2002/0183750 A1 | 12/2002 | Buhler |
| 2003/0040671 A1 | 2/2003 | Somogyi et al. |
| 2003/0053855 A1 | 3/2003 | Baur |
| 2003/0144669 A1 | 7/2003 | Robinson |
| 2003/0195515 A1 | 10/2003 | Sohngen |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0030395 A1 | 2/2004 | Blunn |
| 2004/0055610 A1 | 3/2004 | Forsell |
| 2004/0133219 A1 | 7/2004 | Forsell |
| 2004/0138663 A1 | 7/2004 | Kosashvili et al. |
| 2004/0138725 A1 | 7/2004 | Forsell |
| 2004/0193266 A1 | 9/2004 | Meyer |
| 2005/0012617 A1 | 1/2005 | DiSilvestro et al. |
| 2005/0034705 A1 | 2/2005 | McClendon |
| 2005/0049617 A1 | 3/2005 | Chatlynne et al. |
| 2005/0055025 A1 | 3/2005 | Zacouto |
| 2005/0065529 A1 | 3/2005 | Liu et al. |
| 2005/0090823 A1 | 4/2005 | Bartimus |
| 2005/0107787 A1 | 5/2005 | Kutsenko |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester ............... A61B 17/7016 606/279 |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0052782 A1 | 3/2006 | Morgan |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0085043 A1 | 4/2006 | Stevenson |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |

(56) References Cited

U.S. PATENT DOCUMENTS

| | | |
|---|---|---|
| 2007/0015622 A1 | 1/2007 | Stauch |
| 2007/0016202 A1 | 1/2007 | Kraft |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0244488 A1 | 10/2007 | Metzger |
| 2007/0255088 A1 | 11/2007 | Jacobson et al. |
| 2007/0264605 A1 | 11/2007 | Belfor et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0048855 A1 | 2/2008 | Berger |
| 2008/0051784 A1 | 2/2008 | Gollogly |
| 2008/0065181 A1 | 3/2008 | Stevenson |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0062798 A1 | 3/2009 | Conway |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112262 A1 | 4/2009 | Pool |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0254088 A1 | 10/2009 | Soubeiran |
| 2009/0275984 A1 | 11/2009 | Kim et al. |
| 2010/0004654 A1 | 1/2010 | Schmitz et al. |
| 2010/0049204 A1 | 2/2010 | Soubeiran |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0121323 A1 | 5/2010 | Pool et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0228167 A1* | 9/2010 | Ilovich ............... A61B 17/7216 601/89 |
| 2010/0228357 A1 | 9/2010 | Stauch |
| 2010/0249782 A1 | 9/2010 | Durham |
| 2010/0249847 A1 | 9/2010 | Jung et al. |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0054473 A1 | 3/2011 | Brigido |
| 2011/0057756 A1 | 3/2011 | Marinescu et al. |
| 2011/0060336 A1 | 3/2011 | Pool et al. |
| 2011/0066188 A1 | 3/2011 | Seme et al. |
| 2011/0098748 A1 | 4/2011 | Jangra |
| 2011/0137347 A1 | 6/2011 | Hunziker |
| 2011/0138948 A1* | 6/2011 | Jimenez ................. F16H 25/20 74/424.82 |
| 2011/0152725 A1 | 6/2011 | Demir et al. |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0230883 A1 | 9/2011 | Zahrly |
| 2011/0238126 A1 | 9/2011 | Soubeiran |
| 2011/0257487 A1* | 10/2011 | Thalgott ................. A61B 17/02 600/208 |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0035661 A1 | 2/2012 | Pool et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0136356 A1 | 5/2012 | Doherty et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0203282 A1 | 8/2012 | Sachs et al. |
| 2012/0221106 A1 | 8/2012 | Makower et al. |
| 2012/0271353 A1 | 10/2012 | Barry |
| 2012/0283781 A1 | 11/2012 | Arnin |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0079776 A1* | 3/2013 | Zwirkoski ............ A61B 17/683 606/62 |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0142631 A1 | 5/2014 | Hunziker |

(56) References Cited

U.S. PATENT DOCUMENTS

| | | | |
|---|---|---|---|
| 2014/0163664 A1 | 6/2014 | Goldsmith | |
| 2014/0195003 A1 | 7/2014 | Pool | |
| 2014/0236234 A1 | 8/2014 | Kroll et al. | |
| 2014/0236311 A1 | 8/2014 | Vicatos et al. | |
| 2014/0257412 A1 | 9/2014 | Patty et al. | |
| 2014/0277446 A1 | 9/2014 | Clifford et al. | |
| 2014/0296918 A1 | 10/2014 | Fening et al. | |
| 2014/0303538 A1 | 10/2014 | Baym et al. | |
| 2014/0303539 A1 | 10/2014 | Baym et al. | |
| 2014/0324047 A1 | 10/2014 | Zahrly et al. | |
| 2014/0358150 A1 | 12/2014 | Kaufman et al. | |
| 2015/0105782 A1 | 4/2015 | D'Lima et al. | |
| 2015/0105824 A1 | 4/2015 | Moskowitz et al. | |
| 2015/0196332 A1 | 7/2015 | Pool | |

FOREIGN PATENT DOCUMENTS

| | | | |
|---|---|---|---|
| DE | 1541262 A1 | 6/1969 | |
| DE | 8515687 U1 | 12/1985 | |
| DE | 19626230 A1 | 1/1998 | |
| DE | 19745654 A1 | 4/1999 | |
| DE | 102005045070 A1 | 4/2007 | |
| EP | 0663184 A1 | 7/1995 | |
| EP | 1905388 A1 | 4/2008 | |
| FR | 2901991 A1 | 12/2007 | |
| FR | 2900563 B1 | 8/2008 | |
| FR | 2892617 B1 | 9/2008 | |
| FR | 2916622 B1 | 9/2009 | |
| FR | 2961386 B1 | 7/2012 | |
| JP | H0956736 | 3/1997 | |
| JP | 2002500063 A | 1/2002 | |
| WO | WO1998044858 A1 | 1/2002 | |
| WO | WO1999051160 A1 | 1/2002 | |
| WO | WO2001024697 A1 | 1/2002 | |
| WO | WO2001045485 A3 | 1/2002 | |
| WO | WO2001045487 A2 | 1/2002 | |
| WO | WO2001067973 A2 | 1/2002 | |
| WO | WO2001078614 A1 | 1/2002 | |
| WO | 2006090380 A2 | 8/2006 | |
| WO | 2007025191 A1 | 3/2007 | |
| WO | 2007118179 A2 | 10/2007 | |
| WO | 2007144489 A2 | 12/2007 | |
| WO | 2008003952 A1 | 1/2008 | |
| WO | WO2007015239 A3 | 1/2008 | |
| WO | 2008040880 A2 | 4/2008 | |
| WO | WO2007013059 A3 | 4/2009 | |
| WO | 2011018778 A1 | 2/2011 | |
| WO | WO2011116158 A3 | 1/2012 | |
| WO | WO2013119528 A1 | 8/2013 | |
| WO | WO2014040013 A1 | 3/2014 | |

OTHER PUBLICATIONS

International Search Report for PCT/US2012/024691, ISA, dated Aug. 29, 2012, pp. 4.
Written Opinion for PCT/US2010/047842, ISA, mailed Nov. 4, 2010, pp. 6.
Written Opinion for PCT/US2012/024691, ISA, dated Aug. 29, 2012, pp. 6.
Abe et al., "Experimental external fixation combined with percutaneous discectomy in the management of scoliosis.", Spine, 1999, pp. 646-653, 24, No. 7.
Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.
Amer et al., "Evaluation of treatment of late-onset tibia vara using gradual angulation translation high tibial osteotomy", ACTA Orthopaedica Belgica, 2010, pp. 360-366, 76, No. 3.
Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

(56) References Cited

OTHER PUBLICATIONS

Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. Sl05-Sl15, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511. p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.

(56) References Cited

OTHER PUBLICATIONS

Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 4.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

\* cited by examiner

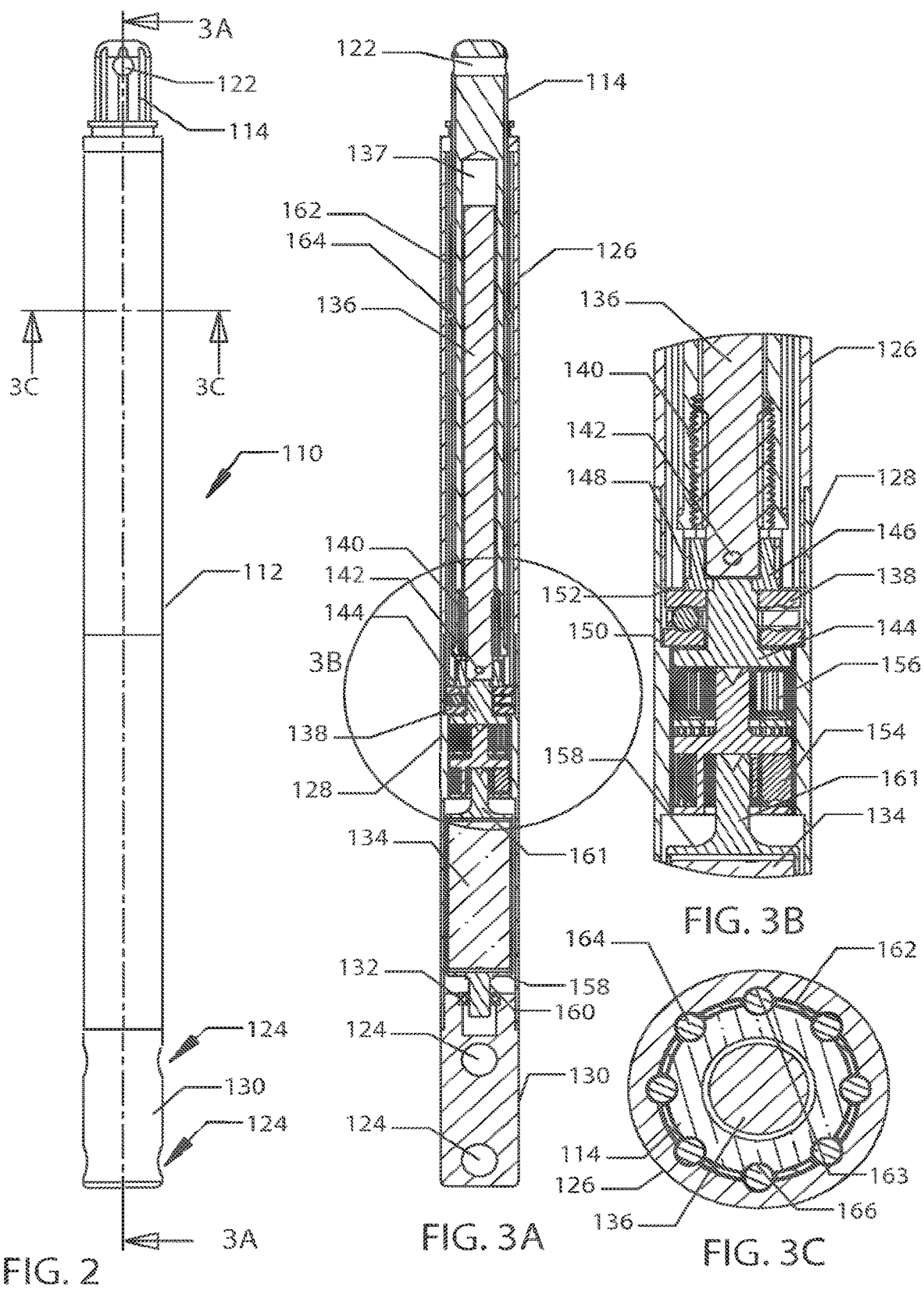

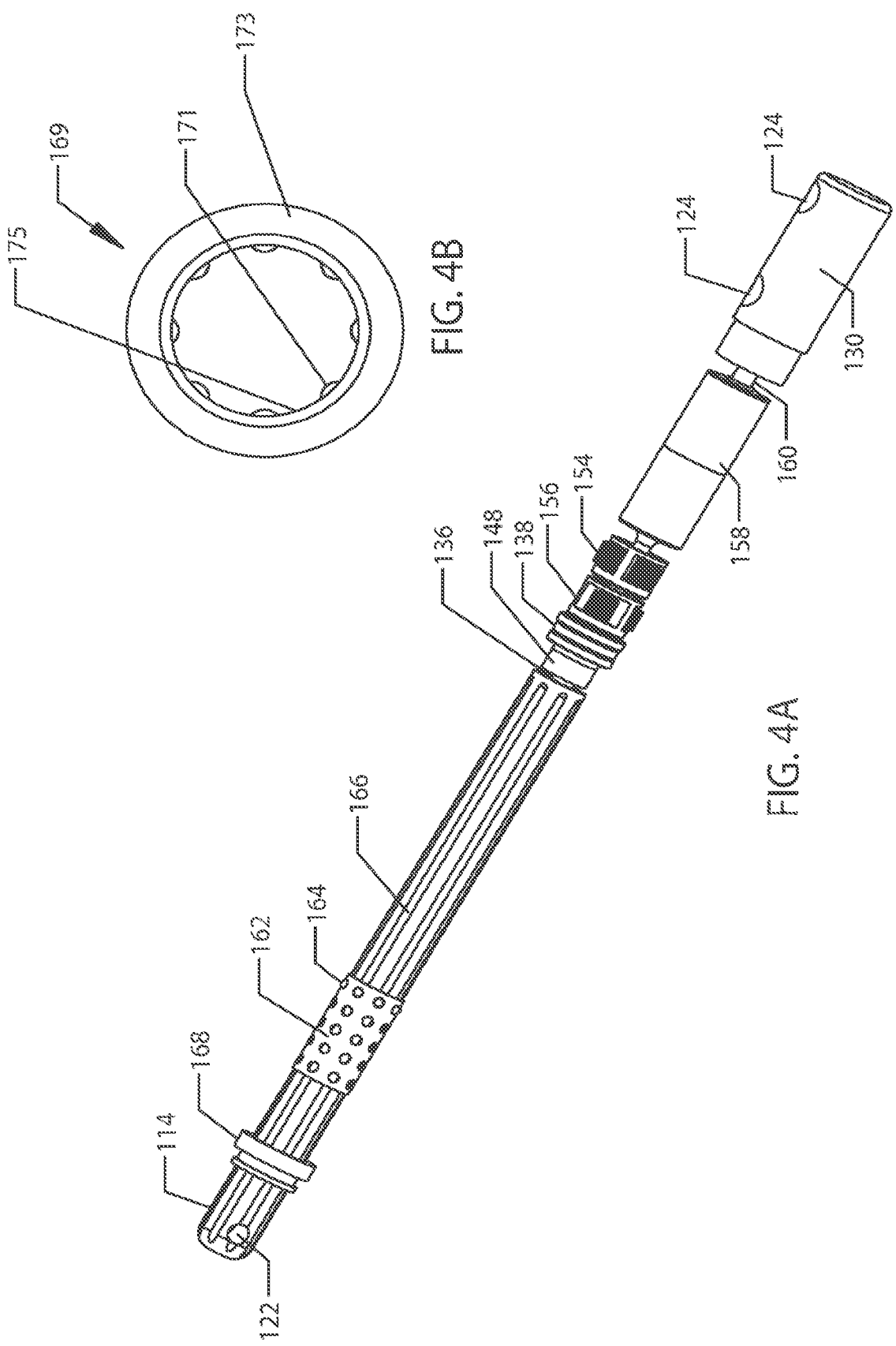

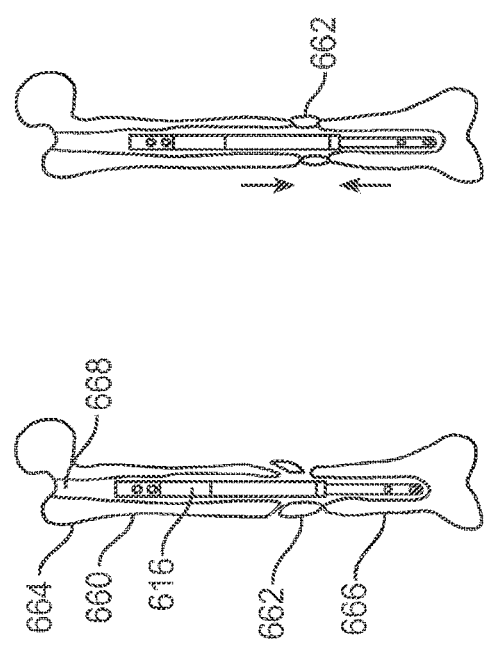
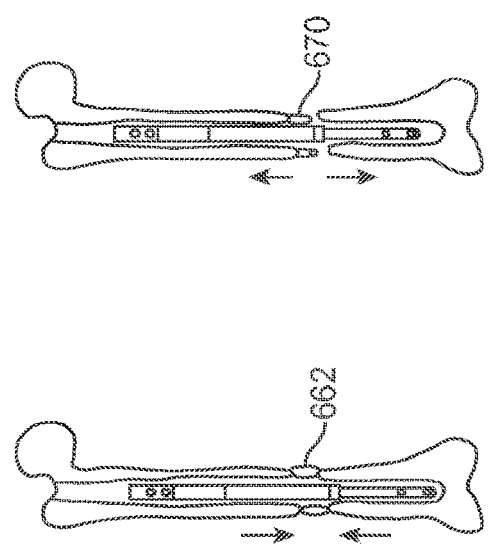
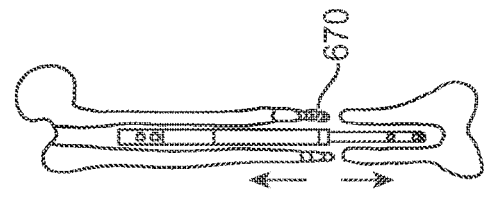
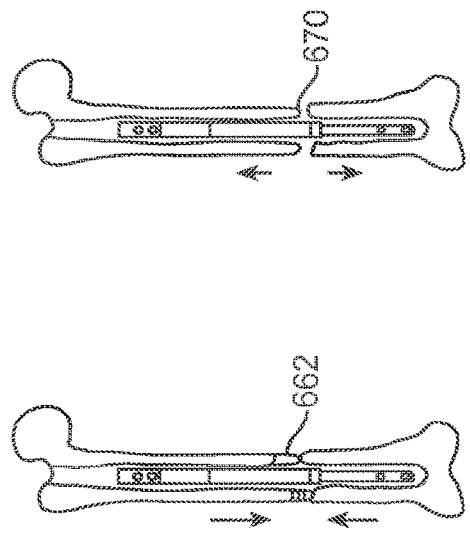
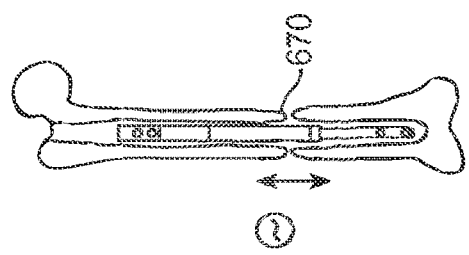
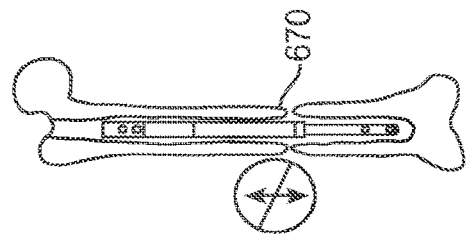
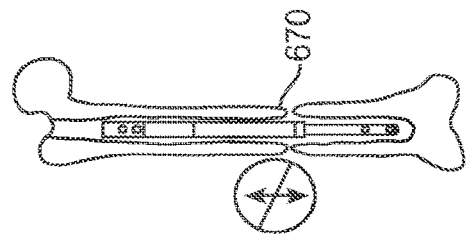

SYSTEM AND METHOD FOR ALTERING ROTATIONAL ALIGNMENT OF BONE SECTIONS

RELATED APPLICATIONS

This application is a continuation of U.S. patent application Ser. No. 16/841,925, filed on Apr. 7, 2020, which is a continuation of U.S. patent application Ser. No. 15/989,672, filed on May 25, 2018, now U.S. Pat. No. 10,646,262, which is a continuation of U.S. patent application Ser. No. 15/207,763, filed on Jul. 12, 2016, now U.S. Pat. No. 10,105,167, which is a continuation of U.S. patent application Ser. No. 14/146,336, filed on Jan. 2, 2014, now U.S. Pat. No. 9,393,117, which is a continuation of U.S. patent application Ser. No. 13/370,966, filed Feb. 10, 2012, now U.S. Pat. No. 8,715,282, which claim the benefit of priority under 35 U.S.C. § 119(c) of U.S. Provisional Pat. Appl. No. 61/442,658, filed Feb. 14, 2011 and U.S. Provisional Pat. Appl. No. 61/472,055, filed Apr. 5, 2011. All of the above applications are incorporated by reference herein and are to be considered a part of this specification. Any and all applications for which a foreign or domestic priority claim is identified in the Application Data Sheet as filed with the present application are hereby incorporated by reference under 37 CFR 1.57.

FIELD

The present disclosure generally relates to medical devices for treating conditions involving the skeletal system and in particular bone fracture applications.

BACKGROUND

Distraction osteogenesis, also known as distraction callotasis and osteodistraction has been used successfully to lengthen long bones of the body. Typically, the bone, if not already fractured, is purposely fractured by means of a corticotomy, and the two segments of bone are gradually distracted apart, which allows new bone to form in the gap. If the distraction rate is too high, there is a risk of nonunion, if the rate is too low, there is a risk that the two segments will completely fuse to each other before the distraction period is complete. When the desired length of the bone is achieved using this process, the bone is allowed to consolidate. Distraction osteogenesis applications are mainly focused on the growth of the femur or tibia, but may also include the humerus, the jaw bone (micrognathia), or other bones. The reasons for lengthening or growing bones are multifold, the applications including, but not limited to, post osteosarcoma bone cancer; cosmetic lengthening (both legs-femur and/or tibia) in short stature or dwarfism/achondroplasia; lengthening of one limb to match the other (congenital, post-trauma, post-skeletal disorder, prosthetic knee joint), non-unions.

Distraction osteogenesis using external fixators has been done for many years, but the external fixator can be unwieldy for the patient. It can also be painful, and the patient is subject to the risk of pin track infections, joint stiffness, loss of appetite, depression, cartilage damage and other side effects. Having the external fixator in place also delays the beginning of rehabilitation.

In response to the shortcomings of external fixator distraction, intramedullary distraction nails have been surgically implanted which are contained entirely within the bone. Some are automatically lengthened via repeated rotation of the patient's limb. This can sometimes be painful to the patient, and can often proceed in an uncontrolled fashion. This therefore makes it difficult to follow the strict daily or weekly lengthening regime that avoids nonunion (if too fast) or early consolidation (if too slow). Lower limb distraction rates are on the order of one millimeter per day. Other intramedullary nails have been developed which have an implanted motor and are remotely controlled. The motorized intramedullary nails have an antenna which needs to be implanted subcutaneously, thus complicating the surgical procedure, and making it more invasive. These devices are therefore designed to be lengthened in a controlled manner, but due to their complexity, may not be manufacturable as an affordable product. Others have proposed intramedullary distractors containing and implanted magnet, which allows the distraction to be driven electromagnetically by an external stator (i.e., a large electromagnet). Because of the complexity and size of the external stator, this technology has not been reduced to a simple and cost-effective device that can be taken home, to allow patients to do daily lengthenings.

Fracture of long bones is often treated with trauma nails. These implants are placed intramedullary to hold the bones together. Often in cases of complex fracture having an irregular break geometry or having multiple bone fragments, it is difficult to secure the nail so that the bone is held at the correct length. Other times it is desired to hold the bone in a manner that apply compression. Every year in the United States, more than 90,000 tibia and femur shaft fractures are defined as complex. Many of these fractures are treated with trauma nails with varying results. Some of the possible complications from the treatment of these complex fractures include: infection, vascular injuries, non-union, neural injury, associated injuries to other bone or joint locations and heterotopic ossification. Also included in the possible complications is the possibility of unmatched bilateral bone lengths.

SUMMARY

In one embodiment, a rotational correction system includes an implant having a first section and a second section, the implant having a rotatable permanent magnet disposed in a housing of the first section, the rotatable permanent magnet mechanically connected to a nut operatively coupled to the second section of the implant. A keyed portion is interposed between the nut and one or more non-linear grooves disposed on an inner surface of the housing. The system includes an external adjustment device comprising at least one rotatable magnet configured to rotate the rotatable permanent magnet of the implant, wherein rotation of the rotatable permanent magnet of the implant in a first direction effectuates a clockwise change in the rotational orientation of the first section relative to the second section and wherein rotation of the rotatable permanent magnet of the implant in a second direction effectuates a counter-clockwise change in the rotational orientation of the first section relative to the second section.

In another embodiment, a rotational correction system includes an implant configured for implantation within a patient, the implant comprising a first section and a second section, the implant having a rotatable permanent magnet disposed in a housing of the first section, the rotatable permanent magnet mechanically connected to nut via a lead screw, the nut operatively coupled to the second section of the implant. A keyed portion is interposed between the nut and one or more non-linear grooves disposed on an inner surface of the housing. The system includes a permanent magnet configured for movement external to the patient, wherein movement of the permanent magnet rotates the rotatable permanent magnet of the implant, thereby modifying the rotational orientation of the first section relative to the second section.

In still another embodiment, a method for changing the rotational orientation of two sections of a long bone of a subject includes forming an entry point in the skin of the subject in proximity to the long bone and at least partially clearing a canal through a center of the long bone. An implant having a first section and a second section is inserted into the canal and the first and second sections are secured to different portions of the long bone, the implant having a rotatable permanent magnet disposed in a housing of the first section, the rotatable permanent magnet mechanically connected to a nut operatively coupled to the second section of the implant, the nut being keyed with respect to non-linear grooves disposed on an inner surface of the housing. An external adjustment device is placed in proximity to the subject's skin, the external adjustment device comprising at least one rotatable magnet and the external adjustment device is operated so that a magnetic field of the at least one rotatable magnet causes the rotatable permanent magnet of the implant to rotate and thereby effectuate a change in the rotational orientation of the first section relative to the second section.

In another embodiment, an intramedullary implant includes: a housing configured to be secured to a first section of bone, the housing including one or more shaft engaging grooves axially extending along an inner surface thereof; a distraction shaft configured to be secured to a second section of bone, the distraction shaft including one or more grooves axially extending along an inner surface thereof; and an actuator disposed within the housing and operably coupled to the distraction shaft, where, in response to rotation of the actuator, the one or more grooves of the distraction shaft engage with the one or more shaft engaging grooves of the housing, causing axial displacement of the distraction shaft relative to the housing.

In another embodiment, an intramedullary implant includes: a housing configured to be secured to a first section of bone, the housing including one or more shaft engaging grooves axially extending along an inner surface thereof; a distraction shaft configured to be secured to a second section of bone, the distraction shaft including one or more grooves axially extending along an inner surface thereof; and one or more ball bearings interposed between the one or more shaft engaging grooves of the housing and the one or more grooves of the distraction shaft, where the one or more ball bearings are configured to rotationally lock the one or more grooves of the distraction shaft relative to the one or more shaft engaging grooves of the housing.

In yet another embodiment, a method of adjusting the first section of the bone with an intramedullary implant is provided. The intramedullary implant includes: a housing configured to be secured to a first section of bone, the housing including one or more shaft engaging grooves axially extending along an inner surface thereof; a distraction shaft configured to be secured to a second section of bone, the distraction shaft including one or more grooves axially extending along an inner surface thereof; and an actuator disposed within the housing and operably coupled to the distraction shaft, where, in response to rotation of the actuator, the one or more grooves of the distraction shaft engage with the one or more shaft engaging grooves of the housing, causing axial displacement of the distraction shaft relative to the housing.

BRIEF DESCRIPTION OF THE DRAWINGS

FIG. 2 illustrates a side view of the intramedullary lengthening device of FIG. 1.

FIG. 3A illustrates a cross-sectional view of the intramedullary lengthening device of FIGS. 1 and 2 taken along the line of 3A-3A of FIG. 2.

FIG. 3B illustrates a detailed view of the intramedullary lengthening device of FIG. 3A from the area of circle 3B.

FIG. 3C illustrates a cross-sectional view of the intramedullary lengthening device of FIGS. 1 and 2 taken along the line 3C in FIG. 2.

FIG. 4A illustrates a view of several of the internal components of the intramedullary lengthening device of the prior FIGS.

FIG. 4B illustrates a lip seal configured for use in the intramedullary lengthening device of the prior FIGS.

FIG. 24A through 24F illustrate the several steps of the implantation, compression and distraction of a variable length nail implanted in a fractured femur.

FIG. 24G illustrates cyclic micromovement being applied by a variable length nail to a fractured femur.

FIG. 24H illustrates a non-movement period between applications of the cyclic micromovement of FIG. 24G.

DETAILED DESCRIPTION

Figure 1:
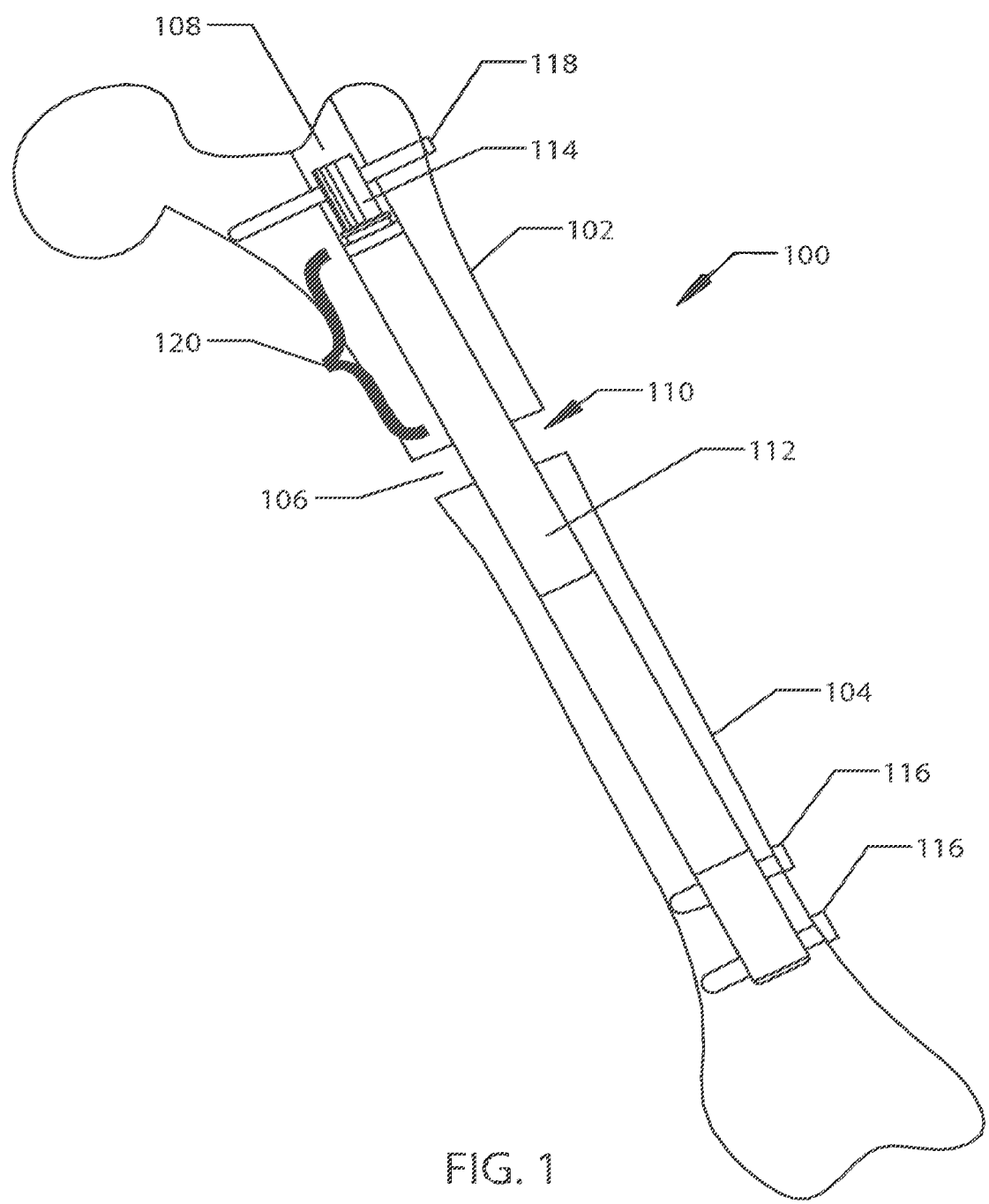
FIG. 1 illustrates side view of an intramedullary lengthening device in place within a bone according to one embodiment.

FIG. 1 illustrates the side view of an intramedullary lengthening device 110 which has been placed through a hole or bore 108 contained within a bone 100. The hole or bore 108 may be made by drilling, reaming and the like and may extend through both cortical bone (at the end) and through cancellous (spongy) bone. The intramedullary lengthening device 110 illustrated in FIG. 1 includes a housing 112 and a distraction shaft 114. In order to grow or lengthen the bone 100, the bone 100 either has a pre-existing separation 106 or is purposely cut or broken to create this separation 106, dividing the bone into a first section 102 and a second section 104. The cut may be done prior to inserting and securing the intramedullary lengthening device 110, or may be done after the device 110 is inserted, for example by use of a flexible Gigli saw. The distraction shaft 114 of the intramedullary lengthening device 110 is attached to the first section 102 using one or more attachment fasteners 118 such as screws. Fasteners 118 other than screws known to those skilled in the art may also be used to secure the distraction shaft 114 to the first section 102 of the bone 100. The housing 112 of the intramedullary lengthening device 110 is secured to the second section 104 of bone 100 using one or more attachment fasteners 116 such as screws. Again, fasteners 116 other than screws may be used to secure the housing 112 to the second section 104 of bone 100.

Over the treatment period, the bone 100 is regularly distracted, creating a new separation 106, into which osteogenesis can occur. Regularly distracted is meant to indicate that distraction occurs on a regular or periodic basis which may be on the order of every day or every few days. An exemplary distraction rate is one millimeter per day although other distraction rates may be employed. That is to say, a typical distraction regimen may include a daily increase in the length of the intramedullary lengthening device 110 by about one millimeter. This may be done, for example, by four lengthening periods per day, each having 0.25 mm of lengthening. The intramedullary lengthening device 110, as disclosed in more detail below, has a magnetic drive system, which allows the distraction shaft 114 to be telescopically extended from the housing 112, thus forcing the first section 102 and the second section 104 of the bone 100 apart from one another. As the distraction process is performed, a portion of the housing 112 is able to slide within the hole or bore 108 of the first section 102 if the housing 112 is located within a displacement section 120 as illustrated in FIG. 1. Alternatively, if the housing 112 is completely contained in second section 104 then there is no sliding of the housing 112 relative to the hole or bore 108. The orientation of the intramedullary lengthening device 110 within the bone 100 may be opposite of that shown in FIG. 1. For example, the distraction shaft 114 may be coupled to the second section 104 of the bone 100 and the housing 112 may be coupled to the first section 102 of the bone 100. For example, the intramedullary lengthening device 110 may be placed retrograde, from a hole or bore starting at the distal end of the bone 100.

Turning to FIGS. 2 through 5, the intramedullary lengthening device 110 has one or more apertures 122 in the distraction shaft 114 through which the fasteners 118 may be placed. Likewise, the housing 112 is attached to or otherwise integrated with an end cap 130 which has one or more apertures 124 through which the fasteners 116 may be placed. The housing 112 of the intramedullary lengthening device 110 includes a magnet housing 128 and a splined housing 126. These housings 126, 128 may be attached to each other by means of welding, adhesive bonding or other joining techniques. The magnet housing 128 is sealably closed at one end (the end opposite the interface with the splined housing 126) by the attachment of the end cap 130. The end cap 130 may be attached to the magnet housing 128 by means of welding, adhesive bonding or other joining techniques. In use, the distraction shaft 114 is driven from the housing 112 by means of a lead screw 136 which turns inside a nut 140 that is secured to an inner surface adjacent to a cavity 137 of the distraction shaft 114. The lead screw 136 is mechanically coupled, in an indirect manner, to cylindrical permanent magnet 134 contained within the magnet housing 128. As explained in more detail below, rotation of the cylindrical permanent magnet 134, which is magnetically driven by an external adjustment device 180 as illustrated in FIG. 6, effectuates rotation of the lead screw 136. Rotation of the lead screw 136 then translates into axial movement of the distraction shaft 114 relative to the housing 128.

Figure 9:
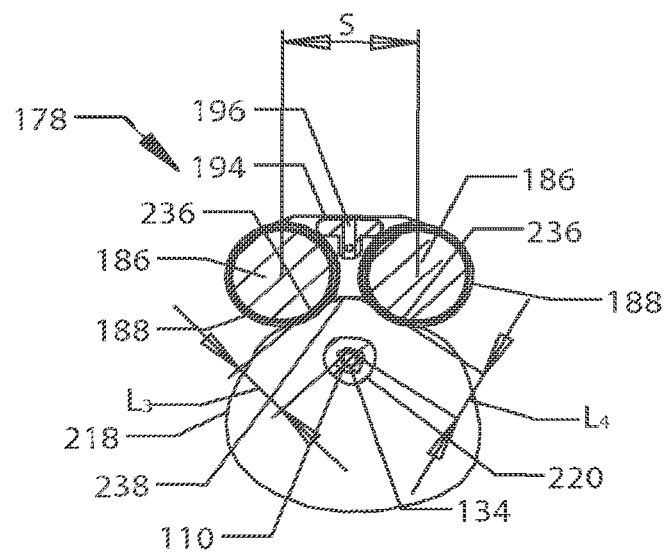
FIG. 9 illustrates a cross-sectional representation of the external adjustment device handpiece of FIGS. 6 and 7 being positioned on a patient's lower thigh.
Figure 19:
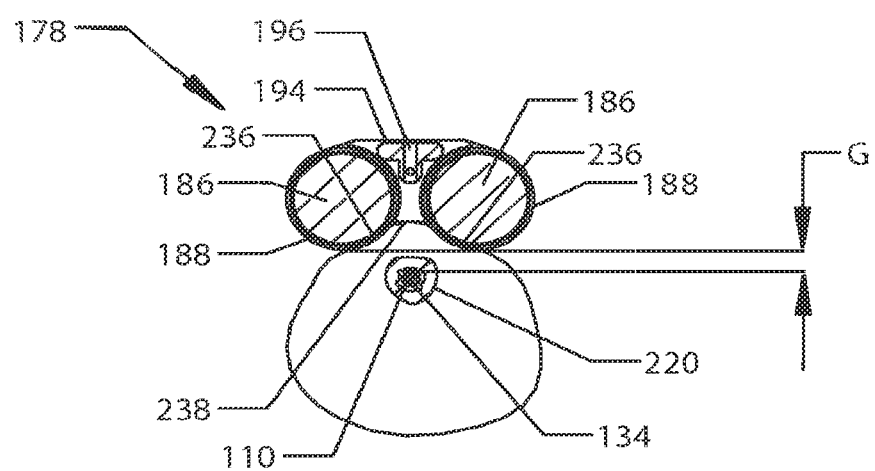
FIG. 19 illustrates a gap (G) between a magnetic handpiece and an intramedullary lengthening device.

Cylindrical magnet 134 is fixedly contained within a magnet casing 158 using, for example, an adhesive such as an epoxy. The magnet casing 158 and cylindrical magnet 134 contained therein rotate relative to the stationary magnet housing 128. The cylindrical magnet 134 may be a rare earth magnet such as Nd-Fe-B and may be coated with Parylene or other protective coatings in addition to being protected within the magnet casing 158, for example hermetically potted with epoxy. The magnet casing 158 contains an axle 160 on one end thereof which attaches to the interior of a radial bearing 132. The outer diameter of the radial bearing 132 is secured to the interior of the end cap 130. This arrangement allows the cylindrical magnet 134 to rotate with minimal torsional resistance. At its other, opposing end, the magnet housing 158 includes an axle 161, which is mechanically coupled to a first planetary gear set 154. The axle 161 includes the sun gear of the first planetary gear set 154, the sun gear turning the planetary gears of the first planetary gear set 154. The first planetary gear set 154 serves to reduce the rotational speed and increase the resultant torque delivery from the cylindrical magnet 134 to the lead screw 136. A second planetary gear set 156 is also illustrated mechanically interposed between the first planetary gear set 154 and the lead screw 136, for further speed reduction and torque augmentation. The number of planetary gear sets and/or the number of teeth in the gears may be adjusted, in order to achieve the desired speed and torque delivery. For example, a lead screw 136 with eighty (80) threads per inch attached to two planetary gear sets of 4:1 gear ratio each inside a 9 mm device with magnet location in the distal femur can achieve at least 100 lb. of distraction force at a greater than average distance or gap from the external device (FIG. 9 or FIG. 19). The planetary gear sets 154, 156 output to a planetary gear output shaft 144. The planetary gear output shaft 144 extends through a thrust bearing 138 and is secured (by welding and the like) to a lead screw coupling cap 146. The lead screw 136 is secured to the lead screw coupling cap 146 by a locking pin 142, which extends transversely through a hole in the lead screw 136 and corresponding holes in the lead screw coupling cap 146. A cylindrical locking pin retainer 148 surrounds the locking pin 142, holding this assembly together. Attaching the lead screw 136 to the rest of the magnet/gear assembly in this manner, assures that the design is not over-constrained, and thus that the lead screw 136 does not gall with the nut 140. In addition, biocompatible grease, for example KRYTOX, may be used on the moving parts (lead screw, nut, bearings, housing, and distraction shaft) in order to minimize frictional losses. The lead screw 136 is able to freely rotate within a cavity 137 of the distraction shaft 114 and thus only needs to engage with the short length of the nut 140. This feature advantageously minimizes frictional losses.

The thrust bearing 138 serves to protect the magnet/gear assembly of the drive from any significant compressive or tensile stresses. The thrust bearing 138 consists of two separate races with ball bearings between the two races. When there is a compressive force on the device, for example, when distracting a bone 100, and thus resisting the tensile strength of the soft tissues, the thrust bearing 138 abuts against a magnet housing abutment or lip 150 located in the magnet housing 128. Additionally, though the device is not typically intended for pulling bones together, there may be some applications where this is desired. For example, in certain compressive nail applications it is the goal to hold two fractured sections of a bone together. Because the bone 100 may have fractured in a non-uniform or shattered pattern, it may be difficult to determine the desired length of the nail until after it is implanted and fully attached. In these situations, it can be easy to misjudge the length, and so a gap may exist between the separate sections or fragments of bone 100. By placing a slightly extended intramedullary device 110 and securing it, the device 110 may be retracted magnetically, after it has been secured within the bone fragments, so that it applies the desired compression between the two fragments. In these compressive nail applications, there would be tensile force on the device 110 and the thrust bearing 138 would abut against a splined housing abutment or lip 152. In both situations, the thrust bearing 138 and a rigid portion of one of the housing sections (e.g., lips 150, 152) take the large stresses, not the magnet/gear assembly of the drive system. In particular, the thrust bearing 138 is sandwiched between the abutment or lip 150 and the abutment or lip 152.

Figure 5:
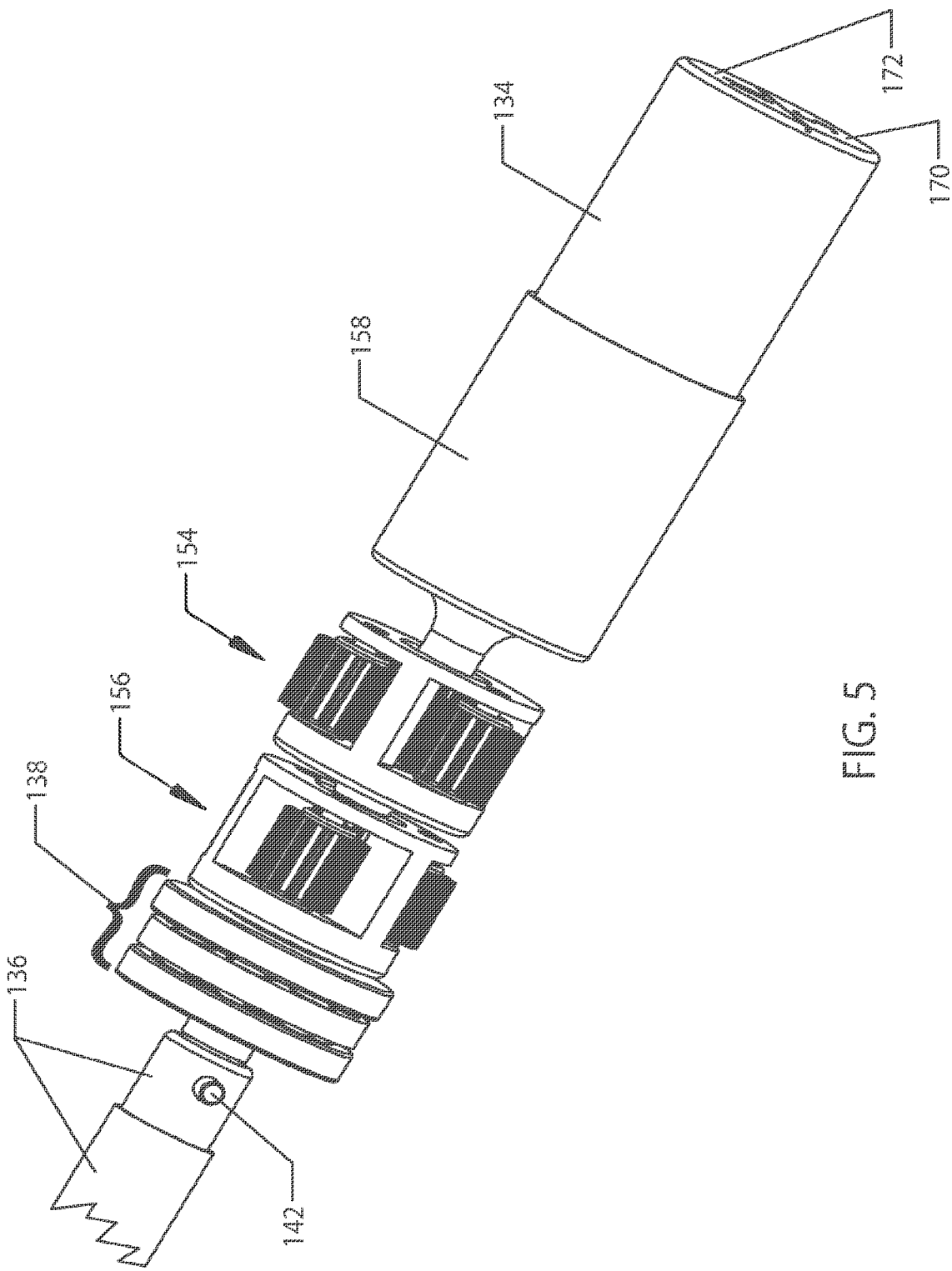
FIG. 5 illustrates a detailed view of several internal components of the drive mechanism of the intramedullary lengthening device of the prior figures.
Figure 6:
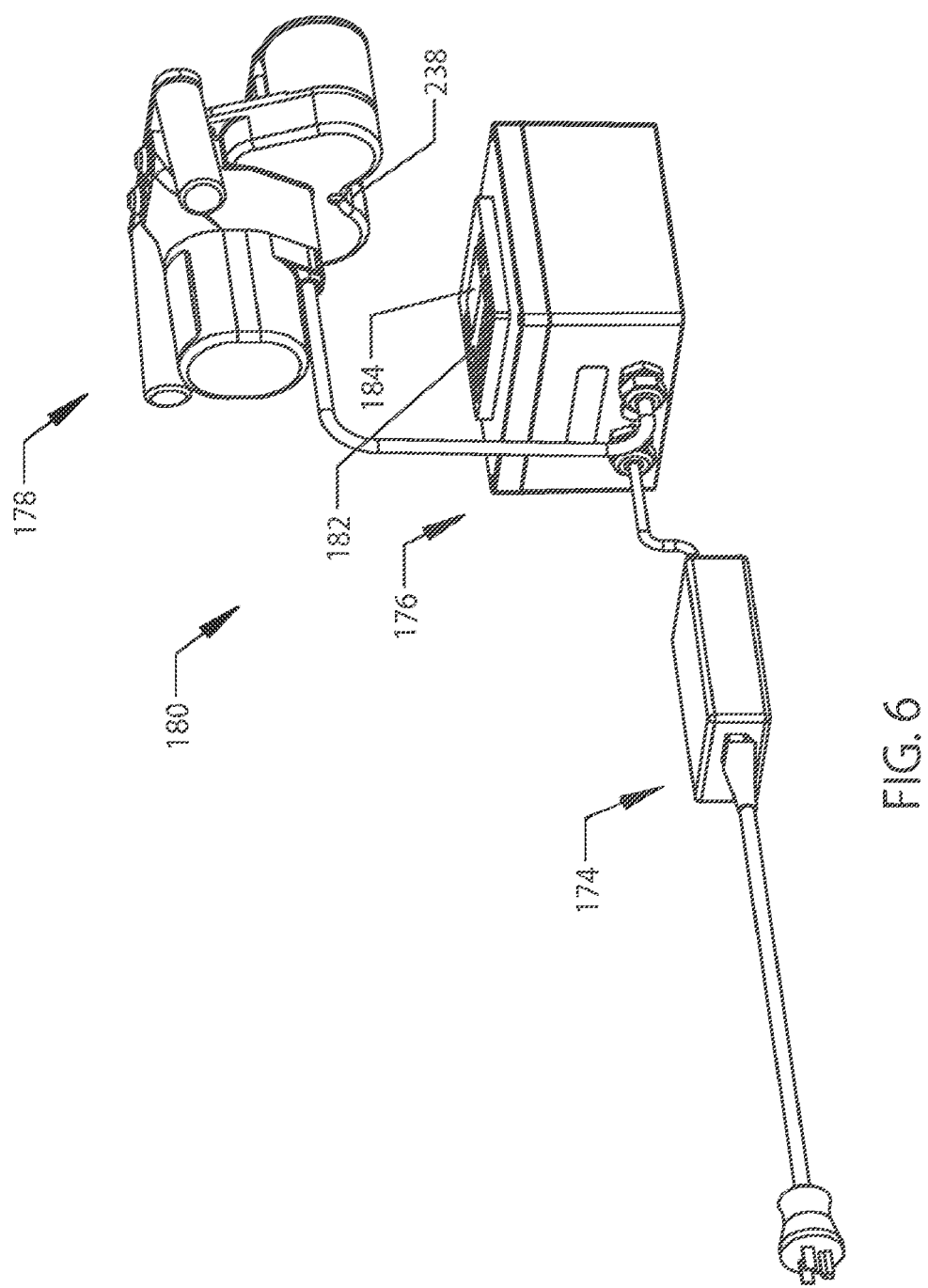
FIG. 6 illustrates a perspective view of an external adjustment device.

Turning specifically to FIGS. 4A and 5, the housing components have been removed to reveal various internal features, including a lip seal flange 168 and linear ball cage 162 that allows sliding of the distraction shaft 114 within the housing 112, and which also keeps the distraction shaft 114 from being able to rotate within the housing 112. This allows full stability of the bone 100. Distraction shaft 114 contains several axial grooves 166 as best seen in FIGS. 3C and FIG. 4A. The grooves 166 have semi-circular indentation cross-sections which allow several balls 164 to roll within them. The balls 164 are trapped within the linear ball cage 162. The splined housing 126 which fits over the balls 164 and linear ball cage 162 has axial grooves 163 (FIG. 3C) along its inner diameter surface that are similar to the axial grooves 166 of the distraction shaft 114. In this regard, the balls 164 and the ball cage 162 are interposed between the distraction shaft 114 and the splined housing 126. Therefore, the balls 164 are held in place by the linear ball cage 162, and mechanically lock the respective grooves to each other, thus impeding rotation of the distraction shaft 114 within the housing 112. However, the balls 164 are able to roll within the linear ball cage 162, thus allowing axial displacement of the distraction shaft 114 in relation to the splined housing 126 of the housing 112 with very low friction. The lip seal flange 168 as seen in FIG. 4A contains a lip seal 169 as seen in FIG. 4B which allows a sliding seal between the distraction shaft 114 and the splined housing 126, thus protecting the inner contents of the entire assembly from the external (e.g., body) environment. The lip seal 169 includes a base portion 173, which seals against the inner diameter of the lip seal flange 168 (and thus the splined housing 126 which is attached to the lip seal flange 168). The lip seal 169 also includes protrusions 171 which slidingly seal against the axial grooves 166 of the distraction shaft 114. Inner surface 175 of the lip seal 169 slidingly seals against the overall outer diameter of the distraction shaft 114. It should also be noted that the lip seal 169 may be made from silicone, EPDM or other rubber materials, and may be coated with silicone oil, to aid in lubricity. Also, the balls, grooves and ball cage may be coated with silicone oil or a liquid perfluorinated polyether such as KRYTOX to aid in lubricity. FIG. 5 shows a portion of the magnet casing 158 removed so that the South pole 170 and North pole 172 of the cylindrical magnet 134 may be illustrated.

FIG. 6 illustrates an external adjustment device 180 which is used to non-invasively distract the intramedullary lengthening device 110 by means of a magnetic coupling which transmits torque. The external adjustment device 180 comprises a magnetic handpiece 178, a control box 176 and a power supply 174. The control box 176 includes a control panel 182 having one or more controls (buttons, switches or tactile, motion, audio or light sensors) and a display 184. The display 184 may be visual, auditory, tactile, the like or some combination of the aforementioned features. The external adjustment device 180 may contain software which allows programming by the physician. For example, the physician may desire that the patient take home the external adjustment device 180 in order that the patient or member of the patient's family or friends make daily distractions of the intramedullary lengthening device 110 implanted in the patient. However, the physician is able to keep the person operating the external adjustment device 180 from over distracting the patient by programming this into the control box 176. For example, the physician may pre-program the control 176 box so that only one (1) mm of distraction is allowed per day. The physician may additionally pre-program the control box 176 so that no more than 0.5 mm may be distracted during any two hour period, or that no more than 0.25 mm may be retracted during a five minute period. Settings such as these may serve to assure that the patient would not be capable of causing severe damage to the bone or tissue, nor disrupt the lengthening process.

Preferably, such instructions or limits may be pre-programmed by the physician or even the manufacturer in a secure fashion such that user cannot alter the pre-programmed setting(s). For example, a security code may be used to pre-program and change the daily distraction limit (or other parameters). In this example, the person operating the external adjustment device 180 will not be able to distract more than one (1) mm in a day (or more than two mm in a day), and will not have the security code to be able to change this function of the external adjustment device 180. This serves as a useful lockout feature to prevent accidental over-extension of the intramedullary lengthening device 110. The safety feature may monitor, for example, rotational movement of magnets 186 (FIG. 7) of the external adjustment device 180, described in more detail below, or the safety feature may monitor rotation of the cylindrical magnet 134 in the intramedullary lengthening device 110, via non-invasive sensing means.

Figure 7:
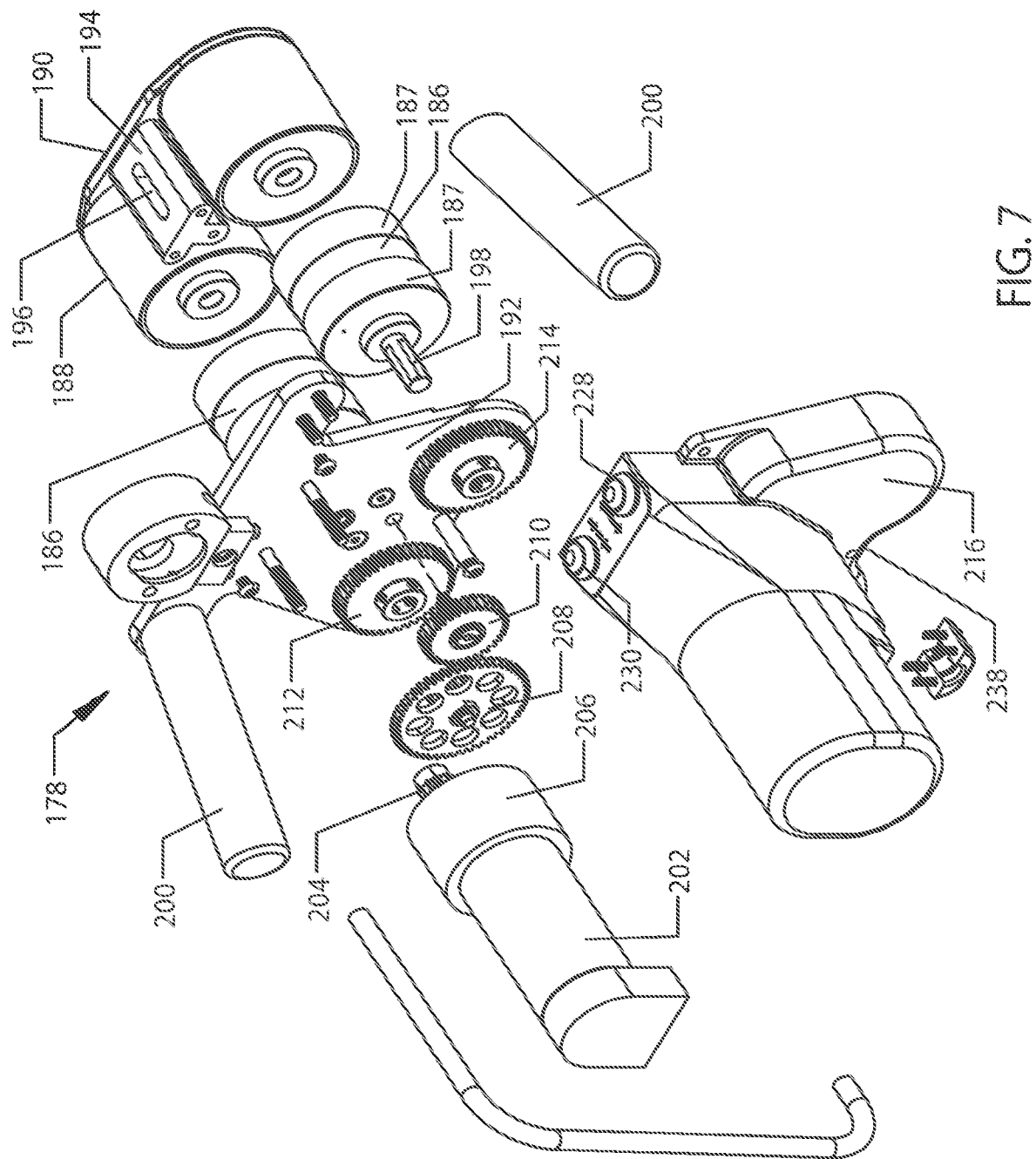
FIG. 7 illustrates an exploded view of the magnetic handpiece of the external adjustment device of FIG. 6.

FIG. 7 shows an exploded view of the magnetic handpiece 178 of the external adjustment device 180, in order to elucidate the manner that the magnets 186 of the external adjustment device 180 serve to cause the cylindrical magnet 134 of the intramedullary lengthening device 110 to turn. As seen in FIG. 7, there are two (2) permanent magnets 186 that have a cylindrical shape. The magnets 186 are made from rare earth magnets. The magnets 186 may have the same radial two pole configuration as the cylindrical magnet 134 seen in FIG. 5. The magnets 186 are bonded or otherwise secured within magnetic cups 187. The magnetic cups 187 include a shaft 198 which is attached to a first magnet gear 212 and a second magnet gear 214, respectively. The orientation of the poles of each the two magnets 186 are maintained in relation to each other by means of the gearing system (by use of center gear 210, which meshes with both first magnet gear 212 and second magnet gear 214). For example, it may be desired that the south pole of one of the magnets 186 is facing up whenever the south pole of the other magnet 186 is facing down. This arrangement, for example, maximizes the torque that can be placed on the cylindrical magnet 134 of the intramedullary lengthening device 110.

The components of the magnetic handpiece 178 are held together between a magnet plate 190 and a front plate 192. Most of the components are protected by a cover 216. The magnets 186 rotate within a static magnet cover 188, so that the magnetic handpiece 178 may be rested directly on the patient, while not imparting any motion to the external surfaces of the patient. Prior to distracting the intramedullary lengthening device 110, the operator places the magnetic handpiece 178 over the patient near the location of the cylindrical magnet 134 as seen in FIG. 9. A magnet standoff 194 that is interposed between the two magnets 186 contains a viewing window 196, to aid in the placement. For instance, a mark made on the patient's skin at the appropriate location with an indelible marker may be viewed through the viewing window 196. To perform a distraction, the operator holds the magnetic handpiece 178 by its handles 200 and depresses a distract switch 228, causing motor 202 to drive in a first direction. The motor 202 has a gear box 206 which causes the rotational speed of an output gear 204 to be different from the rotational speed of the motor 202 (for example, a slower speed). The output gear 204 then turns a reduction gear 208 which meshes with center gear 210, causing it to turn at a different rotational speed than the reduction gear 208. The center gear 210 meshes with both the first magnet gear 212 and the second magnet gear 214 turning them at a rate which is identical to each other. Depending on the portion of the body where the magnets 186 of the external adjustment device 180 are located, it is desired that this rate be controlled, to minimize the resulting induced current density imparted by magnets 186 and cylindrical magnet 134 though the tissues and fluids of the body. For example, a magnet rotational speed of 60 RPM or less is contemplated although other speeds may be used such as 35 RPM or less. At any time, the distraction may be lessened by depressing the retract switch 230. For example, if the patient feels significant pain, or numbness in the area being lengthened.

While the external adjustment device 180 is illustrated herein as including a motor 202 that is used to rotate or drive the magnets 186 in an alternative embodiment, the magnets 186 may be rotated manually. For example, the external adjustment device 180 may include a hand crank or the like that can be manipulated to rotate the magnets 186. In still another embodiment, the external adjustment device 180 may include a single magnet (e.g., permanent magnet) that is manually rotated about an axis by hand. For example, the single magnet may include a hand-held cylindrical magnet that is manually rotated by the user.

Figure 8:
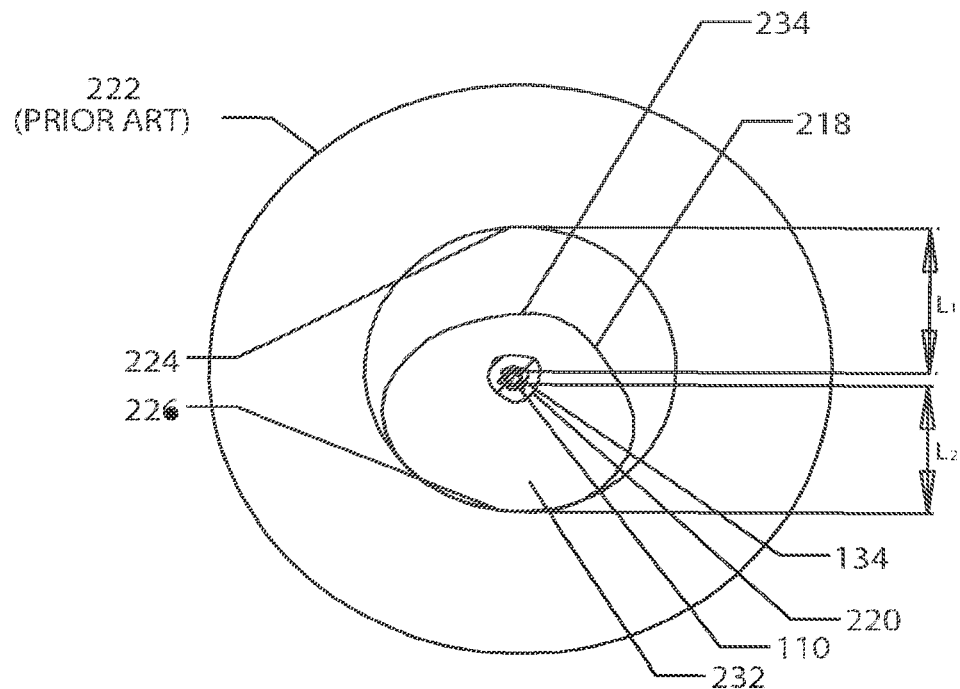
FIG. 8 illustrates a cross-sectional representation of a prior art electromagnetic external device being positioned around a patient's lower thigh.

A cross section of a patient's lower thigh 218 with the intramedullary lengthening device 110 implanted within the femur 220 is shown in FIGS. 8 and 9. In FIG. 9, the magnetic handpiece 178 of the external adjustment device 180 of the invention is shown in position to adjust the cylindrical magnet 134 of the intramedullary lengthening device 110. In FIG. 8, however, a scale depiction of a prior art magnetic stator "donut" 222 demonstrates the comparative efficiency of the two designs (FIG. 8 illustrates an intramedullary lengthening device 110 of the type described herein placed in a "prior art" magnetic stator "donut" 222). Thus, the only part of FIG. 8 that is prior art refers to the magnetic stator donut 222 The prior art magnetic stator "donut" 222 is large, expensive, and difficult to transport to a patient's home for daily adjustments. In addition, the use of a circular cross-section as a one-size-fits-all device is not very efficient because of several reasons: the cross section of most limbs is not circular, the bone is usually not centered within the limb and patients' limbs come in many different sizes. In FIG. 8, the thigh has been placed through the circular hole in the magnetic stator "donut" and the posterior portion 232 of the thigh rests at the lower portion 226 of the magnetic stator "donut" 222. The strength of a magnetic field decreases in accordance with a power (such as the inverse square) of the distance, depending on the complexity of the specific field geometry. Therefore, in any magnetic design, making the distance between the driving magnetic field and the driven magnet as small as possible is desirable. The size of the patient's lower thigh 218 and the decision to how it is placed within the magnetic stator "donut" 222 in FIG. 8 create a geometry so that the distance L1 between the cylindrical magnet 134 and the upper portion 224 of the magnetic stator "donut" 222 is about the same as the distance L2 between the cylindrical magnet 134 and the lower portion 226 of the magnetic stator "donut" 222. However, if the anterior portion 234 of the thigh were instead placed against the upper portion 224 of the magnetic stator "donut" 222, the length L1 would become less while the length L2 would become greater. Because each patient has a different sized limb, and because small limbs like the upper arm as well as large limbs such as the upper leg are desired for treatment, the magnetic stator "donut" 222 of FIG. 8 is almost impossible to optimize. Therefore, an extra-large magnetic field needs to be generated as the standard magnetic field of the device, thus requiring more expense (for the hardware to power this larger field). This in turn means that each patient will be exposed to a larger magnetic field and larger tissue and fluid current density than is really required. It may be desired, in some embodiments, to maintain patient exposure to magnetic fields of 2.0 Tesla or less during operation of the device. It may also be desired, according to another embodiment, to maintain patient exposure of the patient's tissues and fluids to current densities of no more than 0.04 Amperes/meters2 (rms). In addition, because the intramedullary lengthening device 110 is secured to the bone 100, unnecessarily large magnetic fields may cause unwanted motion of the bone 100, for example in any of the radial directions of the cylindrical magnet 134. If the magnetic field is too high, the patient's leg may be moved out of ideal position, and may even cause the patient some annoyance, including pain.

The configuration of the magnetic handpiece 178 of the external adjustment device 180 as shown in FIG. 9 optimizes the ability of the magnets 186 to deliver torque to the cylindrical magnet 134 of the intramedullary lengthening device 110, without exposing the patient to large magnetic fields. This also allows the cylindrical magnet 134 of the intramedullary lengthening device 110 to be designed as small as possible, lowering the implant profile so that it may fit into the humerus, or the tibia and femurs of small stature patients, such as those who might desire cosmetic limb lengthening. As mentioned, a 9 mm diameter intramedullary lengthening device 110 can deliver 100 lb. distraction force, and even 8 mm and 7 mm devices are possible. The alternating orientation of the two magnets 186 (i.e., north pole of one magnet 186 corresponding with south pole of the other magnet 186) creates an additive effect of torque delivery to cylindrical magnet 134, and thus maximizes distraction force for any specific cylindrical magnet 134 size. Also, the separation (S) between the centers of the two magnets 186 (for example 70 mm), and the resulting concave contour 238 (FIGS. 6 and 7), match with the curvature of the outer surfaces of the majority of limbs, thus making the distances L3 and L4 between each of the magnets 186 and the cylindrical magnet 134 as small as possible. This is especially aided by the concave contour 238 of the magnetic handpiece 178. Also, skin and fat may be compressed by the magnet covers 188 causing an indentation 236 on one or both sides which allows the distances L3 and L4 between each of the magnets 186 and the cylindrical magnet 134 to be yet smaller.

Figure 10:
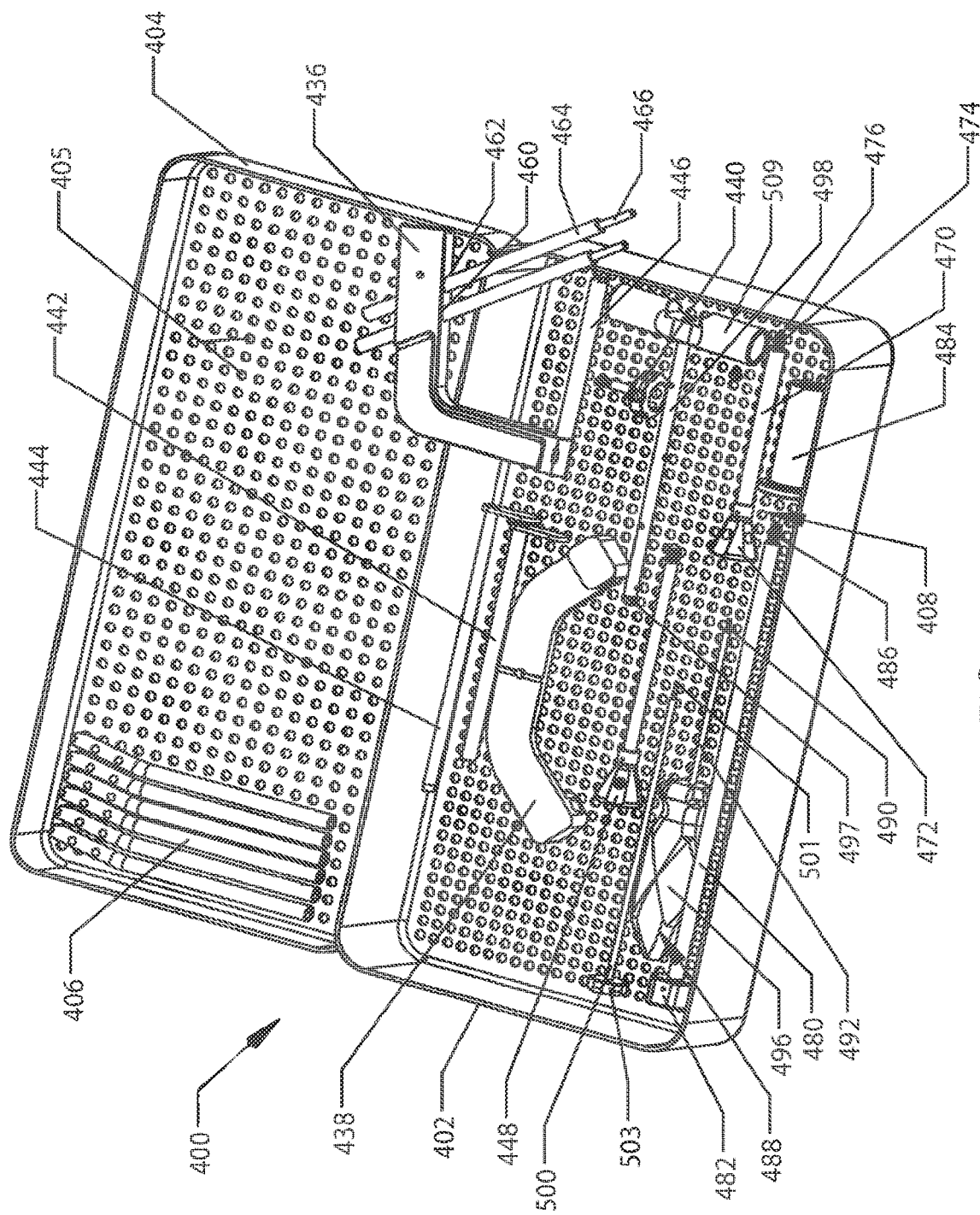
FIG. 10 illustrates a sterilizable kit for use with a modular intramedullary lengthening device.
Figure 11:
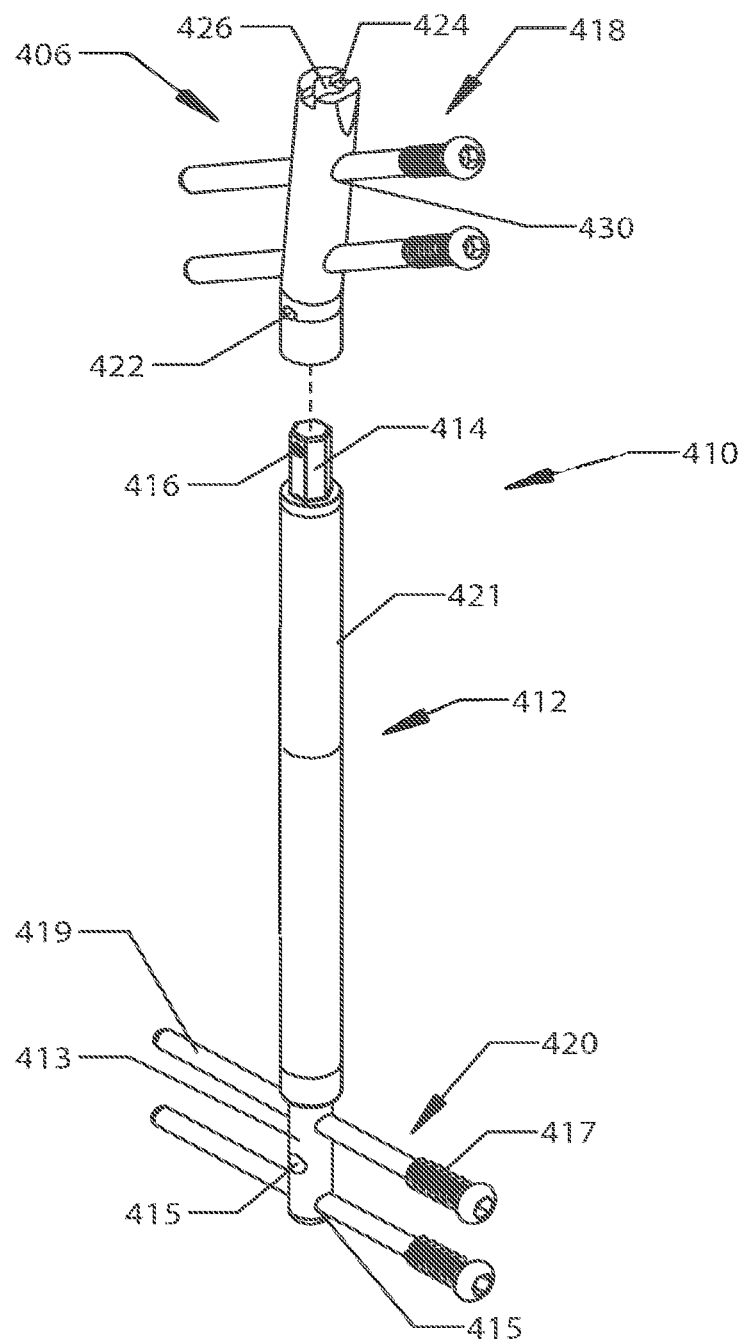
FIG. 11 illustrates a modular intramedullary lengthening device according to one embodiment.

FIG. 10 illustrates a sterilizable kit 400 containing a plurality of extension rods 406 which are configured to be attached to an actuator 412 seen in FIG. 11 in order to construct a modular intramedullary lengthening device 410. In a one embodiment, the actuator 412 is supplied sterile, and the extension rods 406 and the remainder of the contents of the sterilizable kit 400 are sterilizable by autoclave (e.g., steam), Ethylene Oxide or other methods known to those skilled in the art. The sterilizable kit 400 contents includes one or more of the extension rods 406 and accessories 408 for use in the insertion, attachment, adjustment and removal of the modular intramedullary lengthening device 410. The contents are located within a first sterilizable tray 402 and a second sterilizable tray 404. Second sterilizable tray 404 and first sterilizable tray 402 have a plurality of holes 405 to allow gas to enter. Other items in the kit 400 will be described in several of the following figures.

Figure 13:
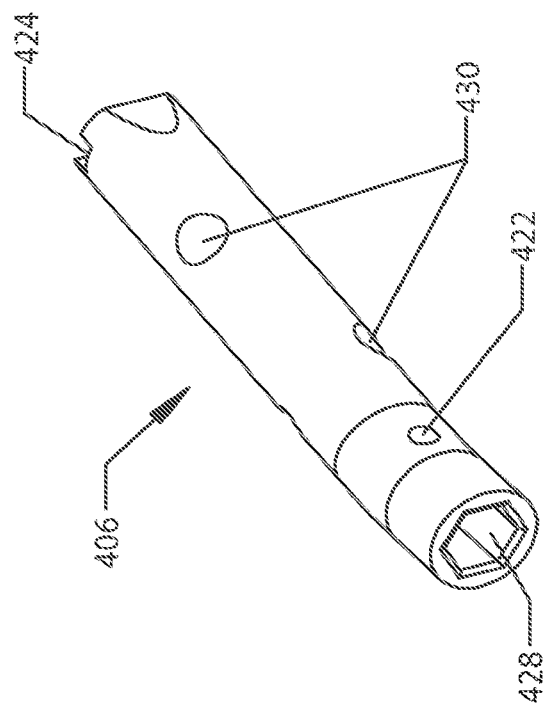
FIG. 13 illustrates an extension rod of the modular intramedullary lengthening device.
Figure 12:
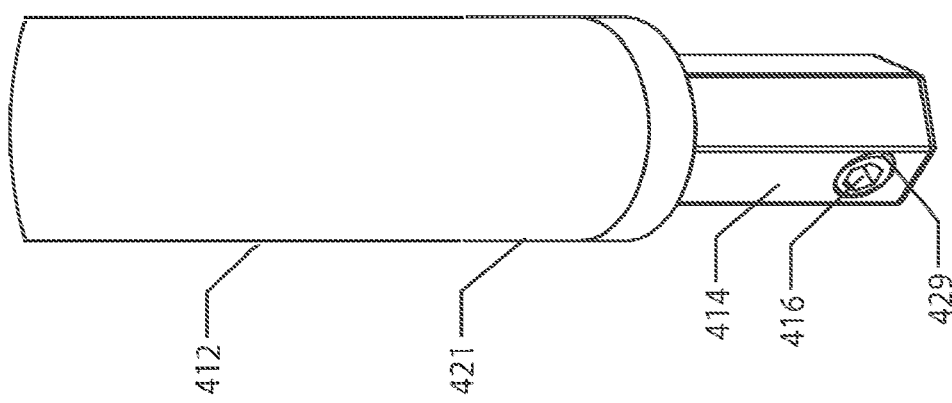
FIG. 12 illustrates one end of the actuator of the intramedullary lengthening device of FIG. 11.
Figure 14:
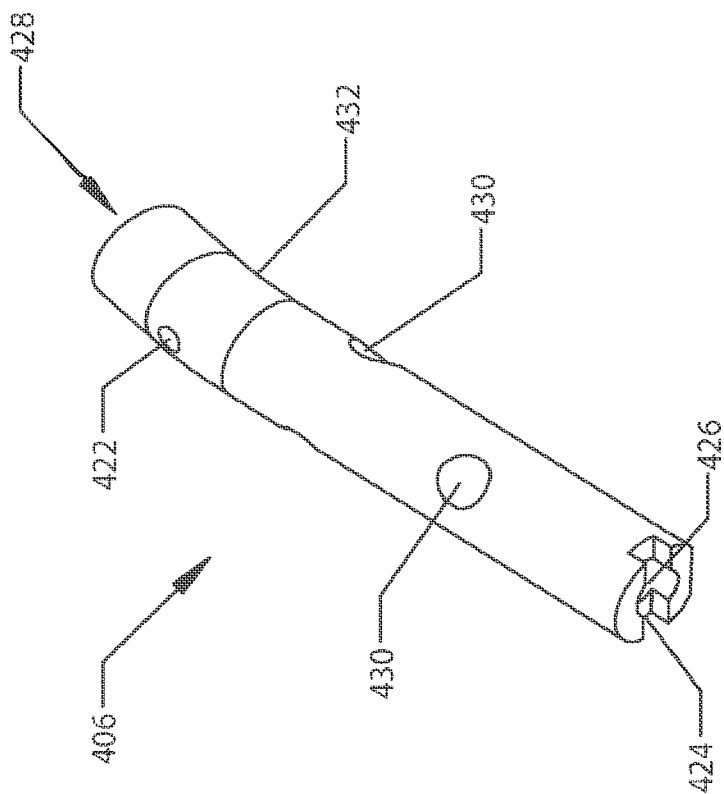
FIG. 14 illustrates a second view of the extension rod of FIG. 13.
Figure 21A:
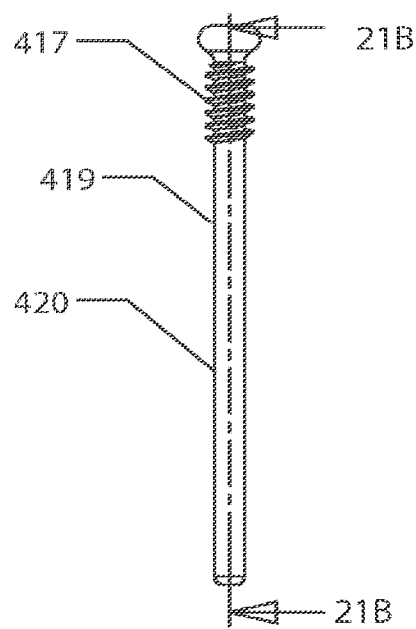
FIG. 21A illustrates a locking screw for use with the intramedullary lengthening device.
Figure 21B:
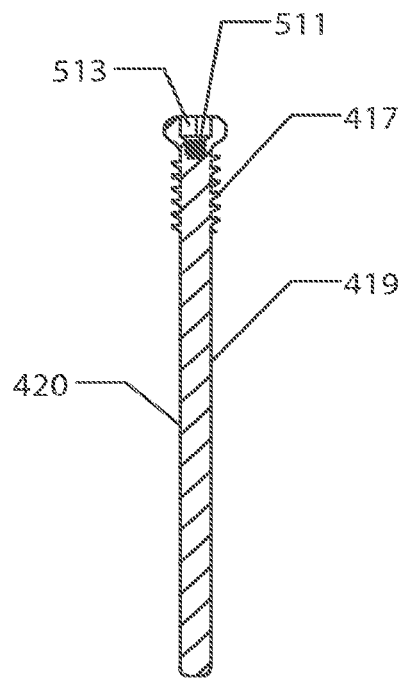
FIG. 21B illustrates the locking screw of FIG. 21A taken along line 21B-21B of FIG. 21A.

Turning to FIG. 11 the assembly of the modular intramedullary lengthening device 410 is shown. The actuator 412 is designed to be placed in the bone of the patient in the opposite orientation than that of the intramedullary lengthening device 110 of FIG. 1. Therefore, the distraction shaft 413 is orientated towards the distal end of the bone (distal is the down direction in the case of FIG. 11). Distal apertures 415 in the distraction shaft 413 allow the placement of distal locking screws 420 or other fasteners. The distal locking screws 420 (FIGS. 21A and 21B) have proximal threads 417 for engaging the bone, while the remainder of the shaft 419 of the distal locking screws 420 is of a constant diameter for maximum strength and stability. At the proximal end 421 of the actuator 412 there is a hexagonally-shaped male hub 414 containing a transverse set screw 416, within a threaded hole 429 of the hexagonal male hub 414 (FIG. 12). The extension rod 406 (FIGS. 13 and 14) has a corresponding hexagonal hole 428 or female end into which the hexagonal male hub 414 of the actuator 412 is placed. The transverse set screw 416 is nested within the threaded hole 429 of the hexagonal male hub 414 so that it does not interfere with the hexagonal hole 428 of the extension rod 406, when they are placed together. There are two set screw holes 422 in the wall of the extension rod 406 which are in line with each other. The actuator 412 and extension rod 406 are placed together so that the set screw holes 422 extend coaxially with the set screw 416. This allows a male hex 490 of a set screw tightening driver, such as the torque limiting driver 488 of FIGS. 10 and 17, to be inserted into a hex hole of the set screw 416. When the torque limiting driver 488 is tightened and ratchets at its set control torque, the other end of the set screw 416, which is either threaded or a non-threaded peg, inserts into the opposite set screw hole 422, thus tightly securing the actuator 412 to the extension rod 406. The set screw holes 422 are sized to allow the male hex 490 to smoothly clear, but the non-threaded peg of the set screw 416 clear very slightly, making a static connection that cannot be easily loosened during implantation. If desired, bone cement may be placed in annulus of set screw hole 422, to even further bond set screw 416. Also, a second screw may be screwed in behind the head of the set screw into the female thread that the set screw 416 was originally nested in. The head of this second screw will add additional resistance to shear failure of the set screw 416. In addition, the second screw can be tightened so that it jams into the set screw 416, thus making back-out of the set screw 416 unlikely. Any non-circular cross-section may be used in place of the hex cross-section, for example a square or oval cross-section.

Proximal locking screws 418 insert through locking screw apertures 430 in the extension rod 406. The extension rod 406 may be straight, or may have a specific curve 432, for example, for matching the proximal end of the femur or tibia. It can be appreciated that the modular arrangement allows the actuator 412 to be attached to one of numerous different models of extension rods 406, having different lengths, curves (including straight), diameters, hole diameters, and angulations. The first sterilization tray 402 may include many of these different extension rods 406, which may be selected as appropriate, and attached to the actuator 412. Because the actuator 412 is supplied sterile, this arrangement is also desirable, as only a single model need be supplied. However, if desired, several models of actuator may exist, for example, different diameters (10.5 mm, 12.0 mm, 9 mm, 7.5 mm) or with different distal screw aperture diameters, configurations or angulations. The preferred configuration for a multitude of patients and different bone types and sizes can be available, with a minimum number of sterile actuator models.

Figure 15:
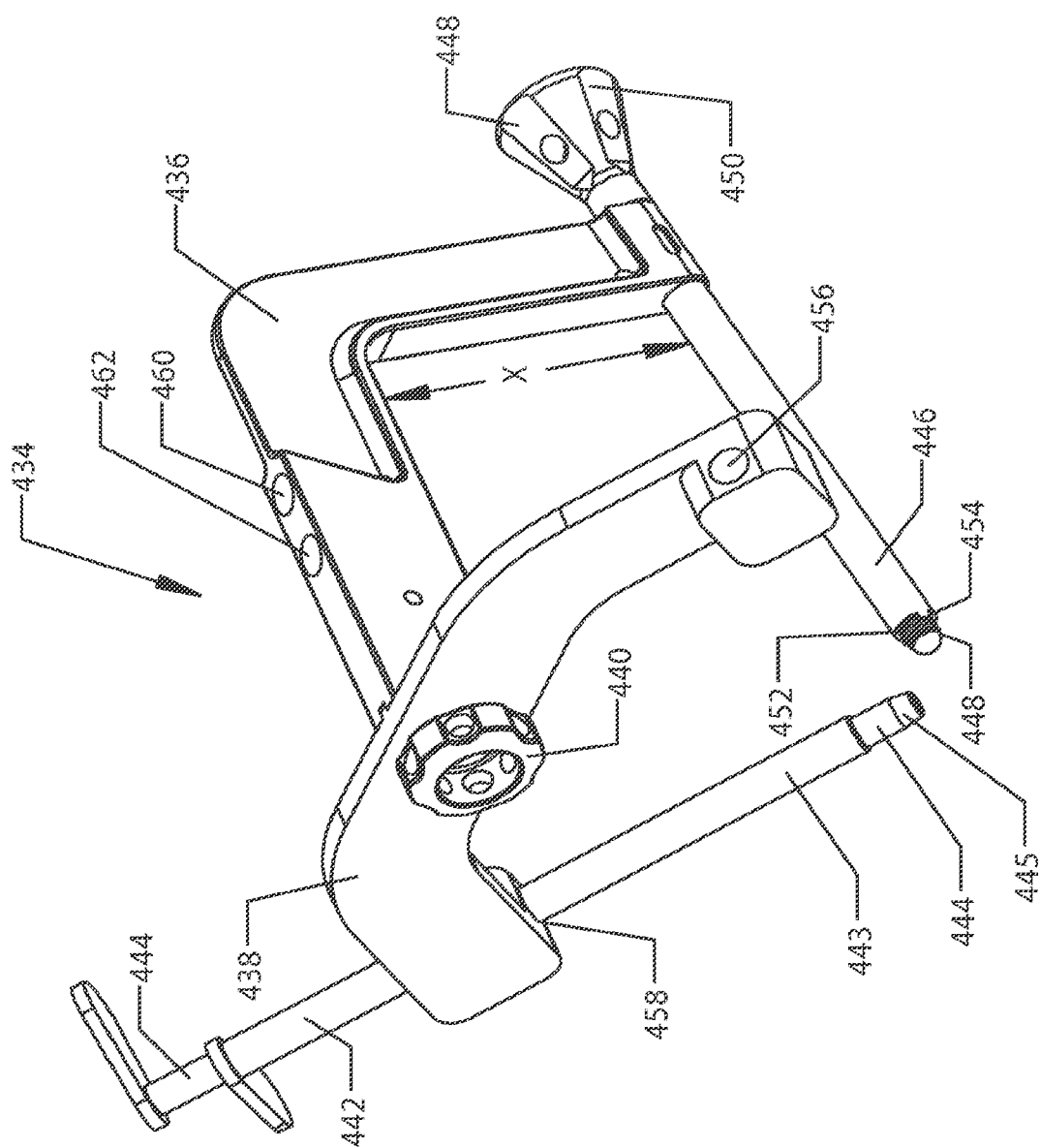
FIG. 15 illustrates a proximal drill guide for insertion and attachment of the modular intramedullary lengthening device.

Turning to FIG. 15, a proximal drill guide 434 is illustrated and is configured for attaching to the modular intramedullary lengthening device 410 to ease its insertion into the intramedullary canal, the drilling of holes in the bone and the attachment of the proximal locking screws 418 to the bone. The proximal drill guide 434 comprises an extension arm 436 attached to a connection tube 446 through which a locking rod 448 is inserted. The locking rod 448 has a locking knob 450 at the proximal end and a male thread 452 at the distal end. In order to temporarily attach the proximal drill guide 434 to the modular intramedullary lengthening device 410, a locking tab 454 of the proximal drill guide 434 is inserted into a locking groove 424 of the extension rod 406 and the locking knob 450 is turned, threading the male thread 452 of the locking rod 448 into a female thread 426 of the extension rod 406. Prior to the procedure a drill guide extension 438 is attached via a knob 440 to the extension arm 436. After reaming the medullary canal of the bone to a diameter slightly larger than the outer diameter of the modular intramedullary lengthening device 410 (for example 11 mm), distal end of the modular intramedullary lengthening device 410 is inserted into the medullary canal and the flat proximal surface of the locking knob 450 is hammered with a mallet, allowing the modular intramedullary lengthening device 410 to be inserted to the correct depth. Dimension X is sufficient to clear large thighs or hips (in the worst case femoral application). For example, 8 to 10 cm is appropriate. Once the modular intramedullary lengthening device 410 is in place in the medullary canal, the proximal drill guide 434 is left attached and a guide sleeve 442 is placed through one of the holes 456, 458, 460, 462 and slid so that the distal end 443 reaches the skin of the patient. The drill guide extension 438, extension arm 436 and holes 456, 458, 460, 462 are dimensioned and oriented so that the guide sleeve 442 is oriented at the exact angle to allow drilling and placement of screws through the locking screws holes 430 of the extension rod 406 and through the bone. The skin of the patient is cut and a drill bushing 444 is placed through the incision, with the tapered tip 445 passing through tissue and reaching the bone to be drilled. For example, drills and locking screws may be inserted down the drill bushing 444, or alternatively, drills may be inserted down the drill bushing 444 and then, after the drilling is complete, the drill bushing 444 is removed and proximal locking screw 418 is inserted down the guide sleeve 442. Alternative guide sleeves 464 and drill bushings 466 can be placed through holes 460 and 462, as seen in FIG. 10.

Figure 16:
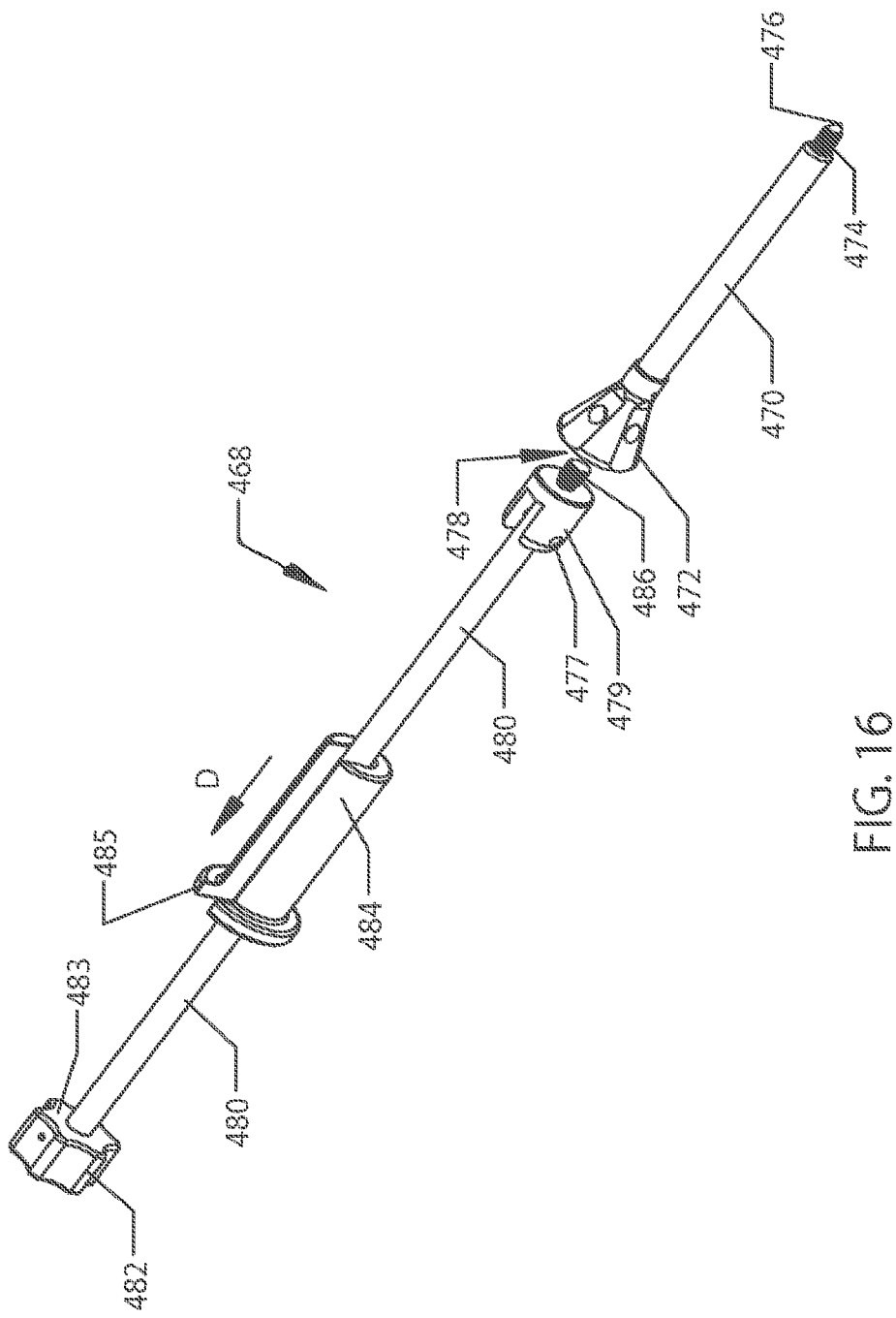
FIG. 16 illustrates a removal tool for removal of the modular intramedullary lengthening device.
Figure 20:
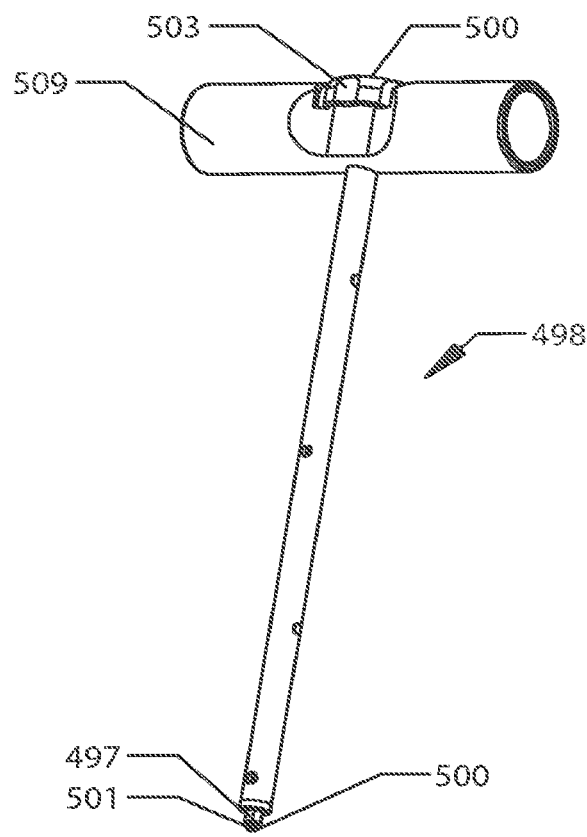
FIG. 20 illustrates a locking screw driver for use with the intramedullary lengthening device.

Turning to FIG. 16, a removal tool 468 is illustrated. The removal tool 468 is used after the distraction period and consolidation period are complete. To remove the modular intramedullary lengthening device 410 from the medullary canal, the skin is incised and bone exposed at the locations of the proximal and distal locking screws 418, 420 and at the proximal end of the modular intramedullary lengthening device 410. A removal rod 470 is connected to the female thread 426 of the extension rod 406 of the modular intramedullary lengthening device 410 by inserting the engagement tip 476 and screwing the male thread 474 into the female thread 426, holding onto the locking knob 472. The locking knob 472 contains a female thread 478 which allows the attachment of a male thread 486 of a removal extension 480, which has an impact knob 482 and removal hammer 484. The male thread 486 is coupled to the removal extension 480 by a pivot 477 of a pivoting base 479. The male thread 486 is secured to the female thread 478 by grasping and turning the impact knob 482. Prior to removing the modular intramedullary lengthening device 410, the proximal and distal locking screws 418, 420 are removed. They may be removed with the use of the locking screw driver 498 (FIGS. 10 and 20), which has a male hex tip 497 to engage the proximal ends of the locking screws 418, 420. A screw capture rod 500 (FIGS. 10 and 20) inserts down the center of the locking screw driver 498 and has a male threaded tip 501. At a deeper portion past the female hex 513 in the locking screws 418, 420 (FIGS. 21A and 21B) is a female thread 511. The male threaded tip 50 I of the screw capture rod 500 threads into the female thread 511 of the locking screws 418, 420, and tightened by using the tightening handle 503 of the screw capture rod 500 which sits at the handle end 509 of the locking screw driver 498 so that once the locking screws 418,420 are removed from the bone, they are still secured to the locking screw driver 498, and will not become prematurely displaced. For example, the locking screws 418, 420 will not be lost or dropped into the patient. The modular intramedullary lengthening device 410 may now be removed from the medullary canal by grasping the removal hammer 484, and moving it quickly in the direction (D) so that hammer impact surface 485 strikes knob impact surface 483. This is done until the modular intramedullary lengthening device 410 is completely removed. It should be noted that locking knob 450 of the proximal drill guide 434 of FIG. 15 also has a female thread (not pictured) so that during the insertion of the modular intramedullary lengthening device 410, if it is desired to remove the device for any reason, the male thread 486 of the removal tool 468 may be attached to the female thread of the locking knob 450, and the removal hammer 484 can be used against the impact knob 482 to remove the modular intramedullary lengthening device 410.

Figure 17:
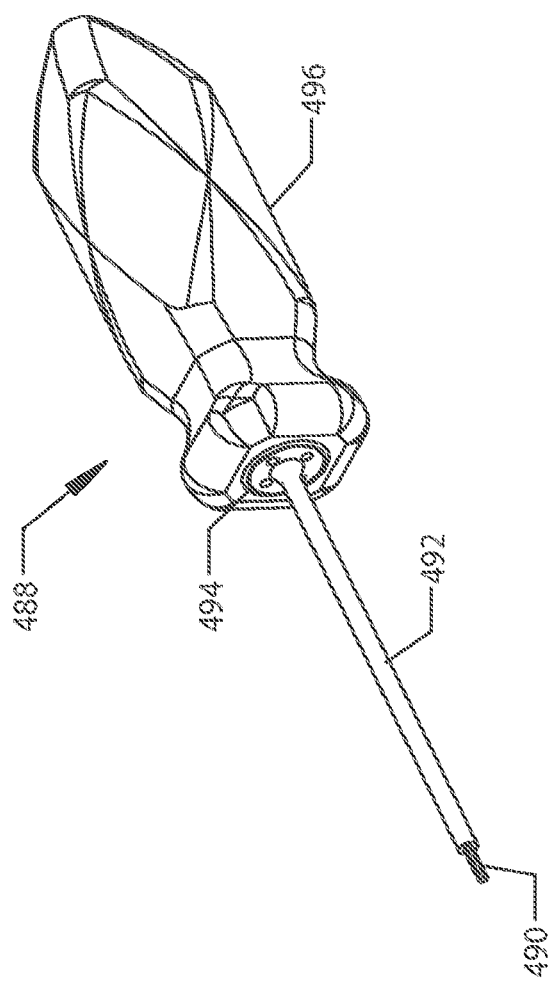
FIG. 17 illustrates a torque limiting driver for attaching the extension rod to the actuator of the modular intramedullary device.

The torque limiting driver 488 of FIG. 17 comprises a handle 496 and a shaft 492 having a torque-specific ratchet 494 connecting them. The male hex tip 490, fits into the hex hole of the set screw 416, or even into the female hex 513 of the locking screws 418, 420. An exemplary ratcheting torque for the set screw 416 is 9 inch-pounds (1.0 Newton-meter), and an exemplary hex size is $\frac{1}{16}$" (1.59 mm).

Figure 18:
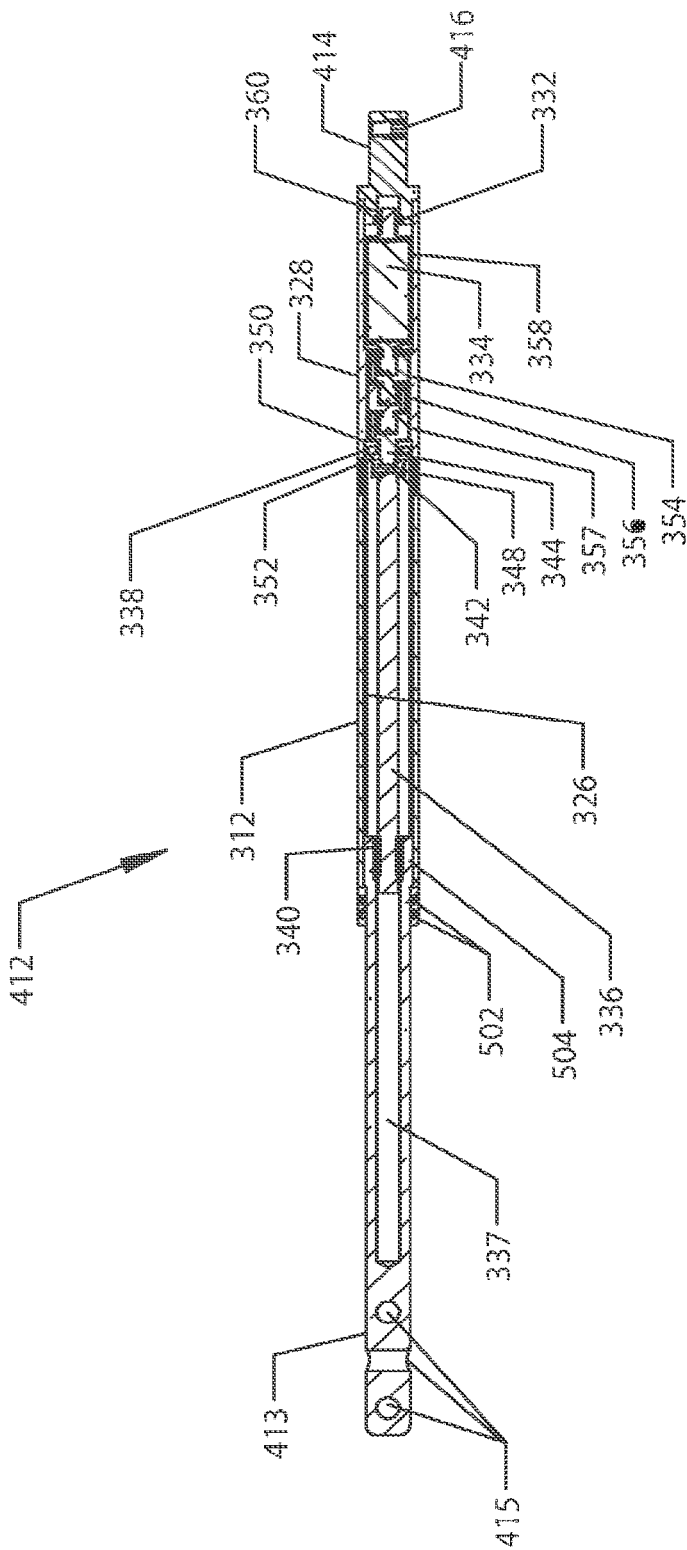
FIG. 18 illustrates a section of the actuator of the modular intramedullary lengthening device.

FIG. 18 illustrates the actuator 412 of FIG. 11 in a sectional view. The distal screw holes 415 are visible in the distraction shaft 413. The distraction shaft 413 is shown in a fully extended position in relation to the housing 312. The cavity 337 has opened to its maximum length. In this embodiment, the distraction shaft 413 has a purely cylindrical surface, and is dynamically sealed to the housing 312 by two o-ring seals 502. The o-ring seals 502 may be made of silicone, EPDM, or other rubber materials, and may be coated with silicone oil, to aid in lubricity. There are four axially extending grooves 326 on the inner wall of the housing 312. Tabs 504 on the end of the distraction shaft 413 fit into these grooves 326 to keep the distraction shaft 413 from being able to rotate with respect to the housing 312. The housing 312 is welded to a magnet housing 328 and the magnet housing 328 is welded to hexagonal male hub 414. The set screw 416 on the hexagonal male hub 414 is used to attach the actuator 412 to the extension rod 406. The cylindrical permanent magnet 334 is cased with epoxy inside magnet casing 358 having an end pin 360. The end pin 360 inserts through radial bearing 332, allowing it to rotate with low friction. As the magnet 334 is rotated by the external magnets, first planetary gear set 354, second planetary gear set 356 and third planetary gear set 357 allow a total reduction of 64:1 (4×4×4). Each gear set allows a 4:1 reduction. Planetary gear output shaft 344 is attached to lead screw 336 by locking pin 342, and locking pin 342 is held in place by cylindrical locking pin retainer 348. Thrust bearing 338 abuts housing abutment or lip 352 and magnet housing abutment or lip 350 (thrust bearing 338 is sandwiched between housing abutment or lip 352 and magnet housing abutment or lip 350). Therefore, thrust bearing 338 abuts housing abutment or lip 352 in tension and magnet housing abutment or lip 350 in compression. It should be noted that the sandwich arrangement allows for some slop or play between the thrust bearing 338 and the housing abutment or lip 352 and the magnet housing abutment or lip 350. Lead screw 336 engages with nut 340, which is secured within distraction shaft 413. With the 64:1 gear reduction of this embodiment, distraction forces of greater than 300 pounds (1334 Newtons) have been consistently achieved with a gap (G in FIG. 19) of 2 inches (5.08 cm) between the magnetic hand piece 178 and the intramedullary lengthening device 110. This is sufficient for distracting a large range of typical patients.

It should be noted that although the embodiments of the intramedullary lengthening devices presented are shown to be used in a preferred orientation (distal vs. proximal), any of these embodiments may be used with the distraction shaft pointing distally or proximally. In addition, the invention may also be applied to distractable bone plates that are not located within the intramedullary canal, but are external to the bone.

An alternative lengthening scheme than those presented above may be also used. For example, one alternative includes the purposeful over-lengthening (to further stimulate growth) followed by some retraction (to minimize pain). For instance, each of four daily 0.25 mm lengthening periods may consist of 0.35 mm of lengthening, followed by 0.10 mm of retraction.

The materials of the accessories 408 are medical grade stainless steel, though other materials of varying densities may be used depending on the desired weight and the required size. The majority of the components of the intramedullary lengthening devices are preferably Titanium or Titanium alloys although some of the internal components may be made from stainless steel.

Intramedullary placed nails are commonly used in trauma of the long bones. Most nails are secured in place with transverse locking screws, much in a similar way to that described in the intramedullary lengthening device described here. In simple fractures it is relatively easy for the orthopedic trauma surgeon to place standard trauma nails correctly, so that the resulting fixture bone is close to the same length and configuration of the bone prior to fracture. However, in complex fractures, it is much more difficult to visually and physically "put the puzzle pieces back together" due to the nature of the fracture and the surrounding soft tissue trauma. Complex fractures many identified using a commonly used classification system such as the Muller AO Classification of Fractures. In addition, to promote healing, it is often desired to place compression between the separate segments of bone initially, for callus formation prior to callus ossification. Also, because it may be difficult to judge the ideal fixture length of the bone during the initial operation, it often would be desirable to adjust the length of the nail, and thus the bone during recovery from the operation, when a true comparison x-ray may be taken (length of bone on treated side vs. length of bone on contralateral side). It may be desired to take this x-ray with patient standing for an idealized comparison. The effect of the complex fracture may be such that a certain amount of distraction osteogenesis will be desired, to bring the fractured leg to a length that matches the other. During a lengthening period, it may be identified that the quality of the fracture callus is inadequate, and that a compression should be applied for a period of time. After this period of time, the lengthening process may be restarted, until the limb length is judged satisfactory. At this point, the nail length would be held constant until ossification is completed.

Figure 22:
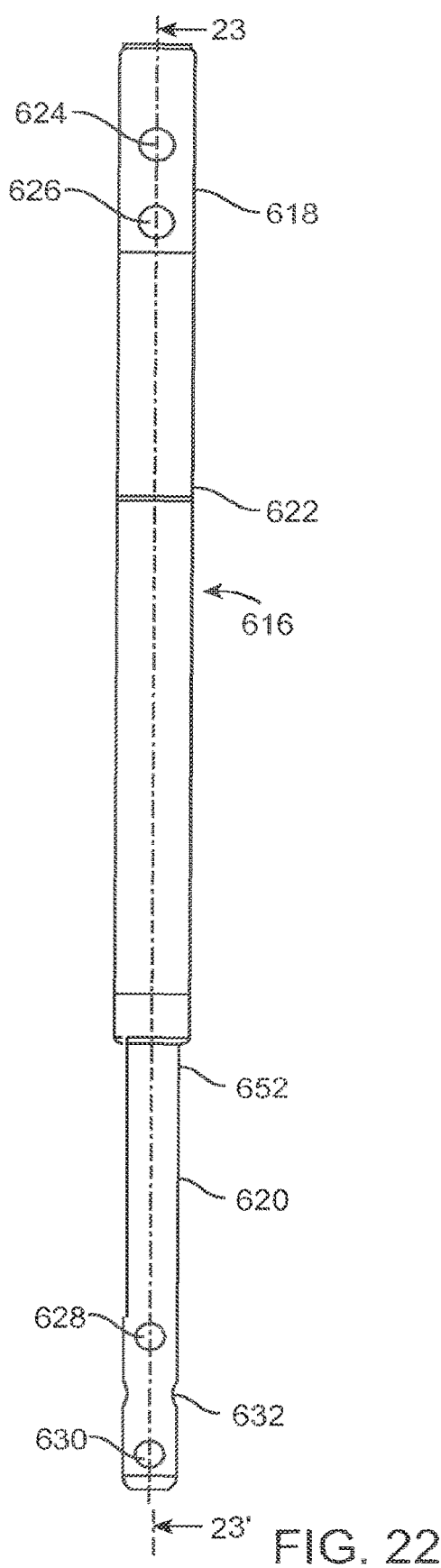
FIG. 22 illustrates a side view of a variable length nail.
Figure 23:
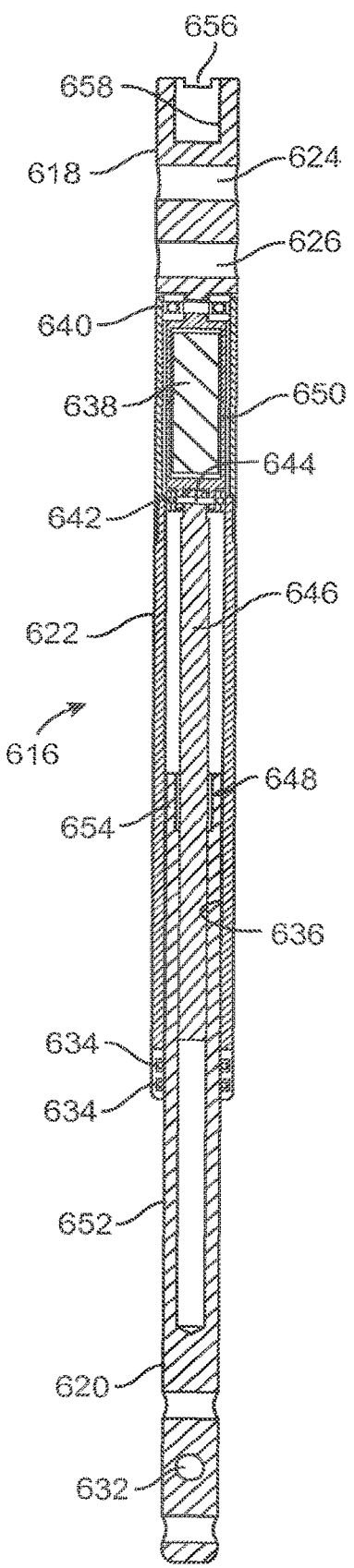
FIG. 23 illustrates a cross-section of the variable length nail of FIG. 22 taken along line 23-23'.

FIGS. 22, 23, and 24A-24H illustrate a variable length nail 616 according to one embodiment. The variable length nail 616 is configured for treating complex fractures of long bones, such as the femur, tibia and humerus. With reference to FIGS. 22 and 23, the variable length nail 616 comprises a first end 618 having holes 624, 626 for accommodating locking screws. The variable length nail 616 also comprises a shaft 652 with a second end 620 having screw holes 628, 630, 632 for accommodating locking screws. The variable length nail 616 also comprises a housing 622 that is secured to or otherwise integrated at one thereof to first end 618. As seen in FIG. 22 and FIG. 23, shaft 652 is telescopically moveable within the housing 622. The shaft 652 is thus able to extend from or retract into the housing 622. A dynamic seal between the housing 622 and the shaft 652 is provided by two o-ring seals 634 as seen in FIG. 23. Still referring to FIG. 23, tabs 654 on the shaft 652 slide within grooves 636 within the housing 622. As in other embodiments disclosed herein, a cylindrical, permanent magnet 638 within a magnet casing 650 is located within the housing 622 and is rotatable between a thrust bearing 640 and a radial bearing 642. In this particular embodiment, there are no gear sets interposed between the cylindrical magnet and the lead screw 646, and the location of the thrust bearing 640 and the radial bearing 642 are reversed in comparison to FIG. 3A and FIG. 18, however the geared configuration and the bearing configurations of FIGS. 3A and 18 are also possible. The non-geared configuration may be preferred, for example, in situations that do not require large distraction forces, and in situations where large adjustments are needed in a short amount of time. This is expected in many of the trauma scenarios described. In addition, a device without the gear sets will be less expensive to manufacture. A pin 644 couples a lead screw 646 to the magnet casing 650. The lead screw 646 interfaces with a nut 648 that resides within a hollowed portion of the shaft 652.

It should be appreciated that the variable length nail 616 is supplied to the user neither in its most retracted (shortest) configuration nor in its most distracted (longest) configuration. For example, in FIGS. 22 and 23, the variable length nail 616 is depicted in the middle of its axial displacement. The variable length nail 616 of FIGS. 22 and 23 has a 10.5 mm housing 622 diameter and a 65 mm total axial displacement. Generally, the variable length nail 616 is configured for at least 5 mm of axial length change in each direction, and in at least some embodiments it is configured for at least 20 mm of axial length change in each direction. It is supplied so that it is about 50% distracted (32.5 mm in the case of FIGS. 22 and 23). Alternatively, it may be desired to supply a device that is only 10% or 25% distracted. Or a model of device may be supplied that is 75% distraction, for example, specifically for patients who require more potential compression than lengthening.

The variable length nail 616 is inserted by making a first hole or incision in the skin of the patient in proximity to the fractured long bone and a canal is at least partially cleared through the center of the long bone. The variable length nail 616 is inserted into the canal and the first and second ends 618, 620 thereof are secured to the different portions of the fractured long bone. The different portions of the fractured long bone may be physically separate from one another prior to insertion. Alternatively, the variable length nail 616 may be inserted into the bone while the different portions are connected to one another. The bone may be subsequent cut using, for instance, a Gigli type wire saw. For insertion of the variable length nail 616, the proximal drill guide 434 may be used. The locking tab 454 of the proximal drill guide 434 is inserted into a locking groove 656 of the variable length nail 616. Additionally, the male thread 452 of the locking rod 448 is tightened into the female thread 658 of the variable length nail 616. The variable length nail 616 can be removed as described in other embodiments using the removal tool 468.

In a complex fracture patient, the surgeon may be unsure whether a standard trauma nail will be successful at fixing the fractured bone without complications and will thus choose to implant the variable length nail 616. FIG. 24A illustrates the variable length nail 616 implanted in a canal 668 of a fractured femur 660. In this patient, the fracture site 662 is between the proximal end 664 and distal end 666 of the femur 660. The variable length nail 616 is secured to the femur 660 at the proximal 664 and distal ends 666 with locking screws (not shown). After the surgery, the hole or incision is allowed to close. After closure, and with the patient awake, the external adjustment device 180 is placed on the thigh of the patient and operated so that the length of the variable length nail 616 is reduced, placing compression on the fracture site 662 as seen in FIG. 24B. This may be done, for example, the day after surgery, when the patient has recovered from anesthesia. Or it may be done a week or so after surgery, when the patient has fully recovered from the surgical procedure. It may also be done after several weeks, after significant tissue healing has occurred. When the fracture callus 670, as seen in FIG. 24C, is in the desired condition, distraction osteogenesis can be started by lengthening the variable length nail 616 (for example 1 mm per day) with the external adjustment device 180. As the distraction period progresses as seen in FIG. 24D, the bone begins to fill in between the distracted portions. At any time, it may be desired to add compression as seen in FIG. 24E at the fracture site 662, and in this case, the external adjustment device 180 is operated to shorten the variable length nail 616. Once again, then the fracture callus 670 is in desired condition, distraction osteogenesis may be resumed as illustrated in FIG. 24 F, and may be continued until the target length of the femur 660 is reached.

An alternative method for using the variable length nail 616 and external adjustment device 180 is depicted in FIGS. 24G and 24H. A technique known as dynamization (also known as controlled early cyclic micromovement) is being applied in FIG. 24G. FIG. 24H represents the rest period between applications of the micromovement. Micromovement has been shown with external fixation devices to enhance callus formation to promote rapid healing and return of bone strength. The user programs the control box 176 of the external adjustment device 180 to cause the magnets 186 of the external adjustment device 180 to cycle in one direction and then the other, such that the variable length nail 616 is lengthened and shortened cyclically (FIG. 24G). For example, a strain of 30% can be achieved by cycling from a 1.0 mm gap between bone sections to a 1.3 mm gap and back again, many times. For example, 500 cycles may be desired over short periods (for example 17 minutes per day). The period should be between 10 minutes per day and one hour per day, to be both feasible in practice and worth performing. It is desirable to keep the strain between 5% and 60%, because at these extremes, the cyclic process has been shown to actually inhibit healing. In between the applications of the cyclic micromovement, the sections of bone are held in place without movement as illustrated in FIG. 24H. It may be desired to perform the cyclic micromovements at a relatively high rate, but a rate of greater than 30 cycles per minute can be effective. It is typically desired to perform some micromovement at the fracture site within the first two weeks after the injury.

Alternatively, the femur depicted in FIGS. 24A-24H could be treated using a retrograde placed variable length nail 616, where the device is inserted through a drilled hole which starts at the distal end of the femur and extends proximally. The same methods can be used on tibia, humerus or even smaller bones.

Figure 25:
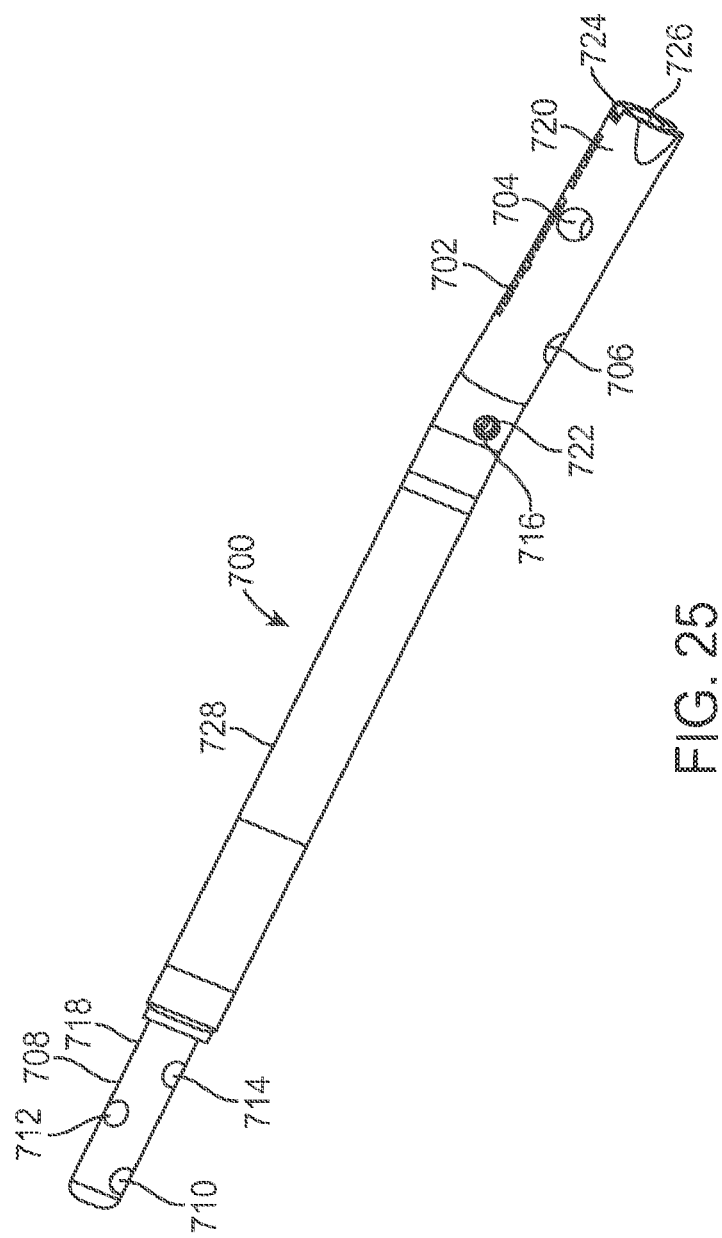
FIG. 25 illustrates an intramedullary rotational correction device according to one embodiment.
Figure 26:
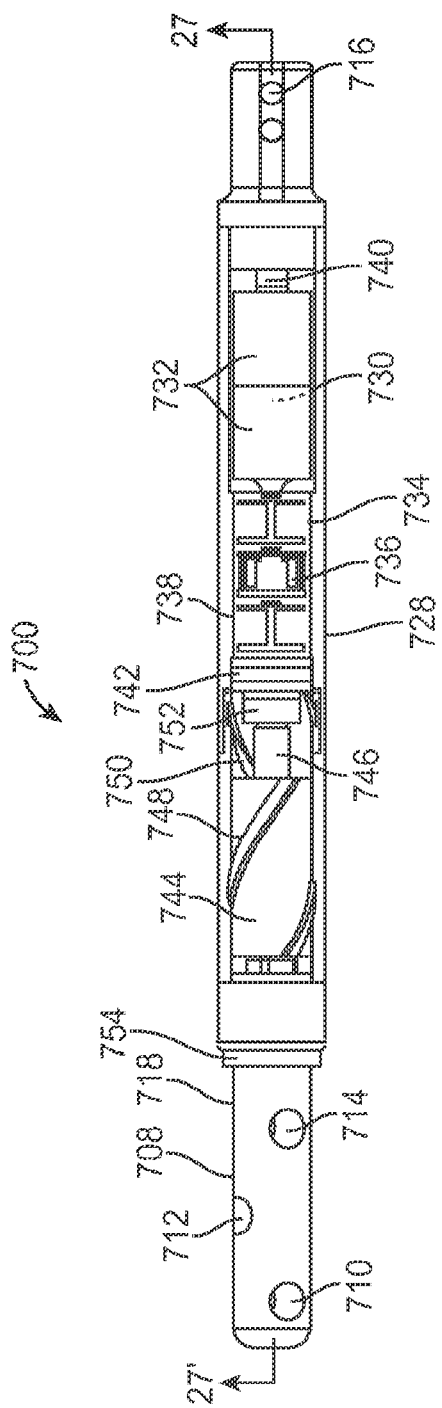
FIG. 26 illustrates a partial sectional view of the rotational correction device.
Figure 27:
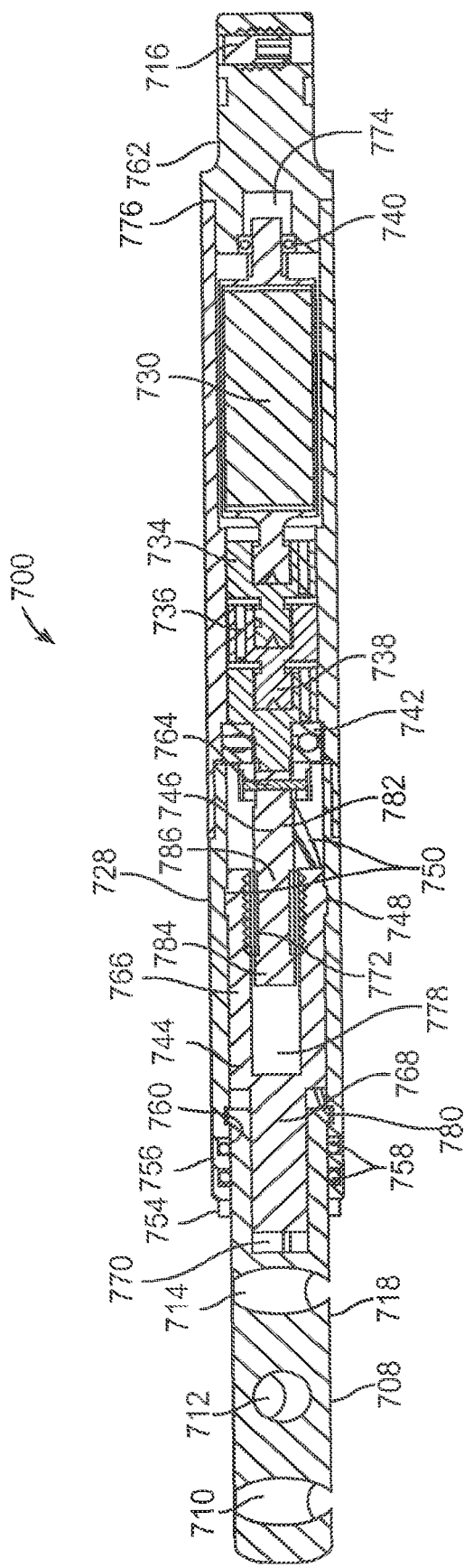
FIG. 27 illustrates a longitudinal section of FIG. 26, taken along the line 27-27'.

In cases of complex trauma, it often occurs that the bone may heal the correct length, or at least close to the desired length, but that one main bone portion may be misaligned angularly (in relation to the longitudinal axis) in relation to another bone portion. It may be desirable to correct this rotation of the bone using an alternative embodiment, as depicted in FIGS. 25 through 27. This embodiment discloses an intramedullary rotational correction device 700 having a first section 702 which is configured to be rotated in relation to a second section 708. The first section 702 comprises a housing 728 and an extension rod 720 which contains holes 704, 706 for placement of fasteners such as locking screws (not shown). The second section 708 comprises a shaft 718 and contains holes 710, 712, 714 for placement of locking fasteners such as screws (not shown). Depicted in FIG. 25, the extension rod 720 is attached to the housing 728 by means of set screw 716, which is accessible through one or more screw holes 722. In this assembly, a locking groove 724 is configured to engage with locking tab 454 of the proximal drill guide 434 of FIG. 15. Also, a female thread 726 is configured to engage with male thread 452 of the locking rod 448 of the proximal drill guide 434.

The mechanism is similar in some ways to the axial distraction mechanisms of other embodiments disclosed herein, but additional features allow the rotation of a lead screw 746 to create controlled angular displacement of the second section 708 (and shaft 718) instead of axial displacement. As seen in FIG. 26, a radially-poled cylindrical magnet 730 and three gear sets 734, 736, 738 are held in the housing 728 (which is exposed in FIG. 26) between a radial bearing 740 and a thrust bearing 742. The radial bearing 740 is held within a hollow portion 774 of an end cap 762 as seen in FIG. 27, with the end cap 762 being secured to the assembly with a weld 776. The cylindrical magnet 730 is contained within a protective magnet casing 732 as seen in FIG. 26. Rotation of the cylindrical magnet 730 causes rotation of each successive gear set 734, 736, 738. An external adjustment device 180 such as those described herein (e.g., FIGS. 6 and 7) may be used rotate the cylindrical magnet 730. Alternatively, a hand crank or the like can be used to rotate the cylindrical magnet 730. In still another embodiment, the external adjustment device 180 may include a single magnet (e.g., permanent magnet) that is manually rotated about an axis by hand to impart rotational movement to the cylindrical magnet 730.

Depicted in FIGS. 26 and 27 are three 4:1 planetary gear sets, which create an overall 64:1 gear ratio. Other gear ratios and numbers of gears sets, however, may be used. The design may also be used without any gear sets or with no gear sets in which case the cylindrical magnet 730 drives the lead screw 746 in a one-to-one fashion. As shown in FIGS. 26 and 27, the output of the third gear set 738 is coupled to the lead screw 746 with a pin 764 which is held in place by a circumferential pin retainer 752 (FIG. 26). The lead screw 746 is engaged with an internal thread 772 of a rotary nut 744. The rotary nut 744 includes a screw engagement portion 766 and an axial sliding hex portion 768. The screw engagement portion 766 of the rotary nut 744 includes one or more non-linear splines 748 which are configured to slide along non-linear grooves 750 within the internal wall of the housing 728. The screw engagement portion 766 of the rotary nut 744 includes the internal thread 772 and a cavity 778 for clearance and free passage of the lead screw 746.

When an external rotating magnetic field, for example from the rotating magnets 186 of the magnetic handpiece 178, is applied to the cylindrical magnet 730, the cylindrical magnet 730 is turned and via transmission with the gear sets 734, 736, 738 turns the lead screw 746 in a first direction. As the lead screw 746 is turned in this first direction within the internal thread 772, the rotary nut 744 extends axially, i.e., away from the cylindrical magnet 730. Because both the non-linear splines 748 and the non-linear grooves 750 have matched helical curve shapes, the rotary nut 744 rotates slightly as it axially extends. For example, the non-linear splines 748 may be configured to extend around the rotary nut 744 a quarter of a turn for every 9.5 mm of length. In concordance, the non-linear grooves 750 may be configured to extend around the interior of the wall of the housing 728 a quarter of a turn for every 9.5 mm of length. Alternatively, the non-linear grooves 750 may be configured to extend a quarter turn for every 18 mm of length. In yet another alternative, the non-linear grooves 750 may be configured to expand a quarter of a turn every 6 mm of length. In this regard, the relative pitch of the non-linear grooves 570 may be adjusted to modify the degree of rotational movement. As yet another alternative embodiment (not shown), the non-linear grooves 750 may be disposed on the external surface of the rotary nut 744 and the non-linear splines 748 may be disposed on the internal wall of the housing 728.

As the rotary nut 744 axially extends and rotates, the axial sliding hex portion 768 slides inside a female hex receptacle 770 of the shaft 718. The axial sliding hex portion 768 and the female hex receptacle 770 are rotationally keyed, each having a hexagonal shape, so that when the axial sliding hex portion 768 turns, the female hex receptacle 770 is turned with it thus turning the shaft 718. This construction allows relative axial sliding, namely, the shaft 718 rotates without any axial extension. The cross sectional shape may be any non-circular shape that is conducive to keying. For example, alternatives include a square shape or an elliptical shape. The shaft 718 is held axially on one end by a retaining collar 754 and on the other end by a lip 780, which in this embodiment is shown integral to the shaft 718, though alternatively, it can be made from a separate piece. An o-ring flange cap 756 is secured to the housing 728 (for example by welding or other direct boding technique) and contains one or more o-ring seals 758 within one or more o-ring flanges 760, thus sealing the internal contents of the housing 728.

The intramedullary rotational correction device 700 is preferably supplied to the customer in a sterile condition (for example by Gamma irradiation), and it may be supplied to the customer in numerous configurations. Three specific configurations will now be described. The supplier may supply the device in each of these configurations, or the supplier may supply the device in a single configuration, and the user may adjust the device into their desired configuration. The intramedullary rotational correction device 700 may be supplied with the internal thread 772 positioned towards a first end 782 of the lead screw 746 (near the pin 764). In this condition, the maximum amount of clockwise rotation may be applied to the second section 708 and shaft 718. Alternatively, the intramedullary rotational correction device 700 may be supplied with the internal thread 772 positioned towards a second end 784 of the lead screw 746. In this condition, the maximum amount of counter-clockwise rotation may be applied to the second section 708 and shaft 718. If it is not known at time of implantation, which direction a rotational discrepancy is possible (or probable), it may be desired to supply (or adjust) the intramedullary rotational correction device 700 so that the internal thread 772 is positioned at an intermediate section 786 of the lead screw 746. In this configuration, either clockwise rotation or counter-clockwise rotation will be available to the user.

In use, a patient is implanted with the intramedullary rotational correction device 700 and locking screws are used to secure the first section 702 and second section 708 to the bone to be treated. If a pre-existing rotational deformity is to be corrected, the implant is chosen with the correct amount of either clockwise or counter-clockwise rotation available, for example, as in the first two conditions described. If instead, the intramedullary rotational correction device 700 is being used as a trauma nail, knowing that the specific type of trauma may cause imprecise fixation, and thus a rotational discrepancy, it may be desired to have both clockwise and counter-clockwise rotation available. In this case, the third condition (allowing both clockwise and counter-clockwise rotation) would be the one desired. In this third condition, after the device is implanted, if the rotational discrepancy is discovered early, before consolidation of the bone fragments, the device may be operated as described to change the rotational orientation of the fragments gradually. If, however, the rotational discrepancy is discovered after the bone fragments have consolidated, an osteotomy may be made to allow the rotation between the fragments to be imparted.

Figure 28:
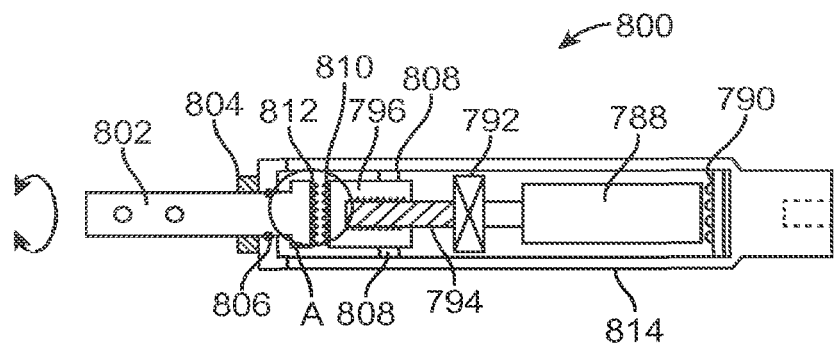
FIG. 28 illustrates a lockable and un-lockable rotational implant according to another embodiment.
Figure 29:
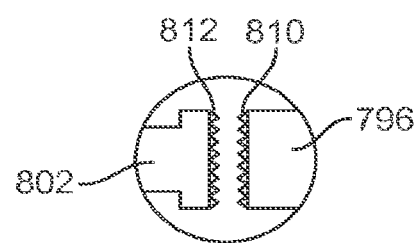
FIG. 29 illustrates a detailed view of region A of FIG. 28.

FIGS. 28 and 29 illustrate a lockable and un-lockable rotational implant device 800 according to another embodiment. The implant 800 has a similar cylindrical magnet/lead screw/nut arrangement to other embodiments described here, except the magnet 788, held between a thrust bearing 790 and a radial ball bearing 792, turns a lead screw 794, moving a nut 796, the nut 796 having teeth 810 on an axial face at the end which interlock with teeth 812 at a matching end of a rotation rod 802 (as best seen in detail section in FIG. 29). The rotation rod 802 is dynamically sealed to a housing 814 by an o-ring seal 806, and held axially in relation to the housing 814 by a retaining collar 804. The nut 796 has anti-rotation ears 808 to keep the nut 796 aligned rotationally with the housing 814. In particular, the anti-rotation ears 808 may interface with corresponding grooves or recesses in the interior surf ace of the housing 814. If it is desired to manually change the rotational orientation of two bone pieces of a patient, the magnet 788 is rotated by a moving magnetic field of an external adjustment device (e.g., external adjustment device 180), so that the teeth 810 of the nut 796 move away from the teeth 812 of the rotation rod 802. Then the teeth 810, 812 are disengaged from each other, the limb can be grasped and one bone piece may be manually rotated with respect to the other bone piece. When the rotational orientation of the two bone pieces is as desired, the magnet 788 is turned in the opposite direction by the external adjustment device 180, so that the teeth 810 of the nut 796 move towards and engage with the teeth 812 of the rotation rod 802, thereby locking the housing 814 and the rotation rod 802 together. An optional slip clutch (not shown) located between the magnet 788 and the lead screw 794 may be used to prevent binding.

Figure 30:
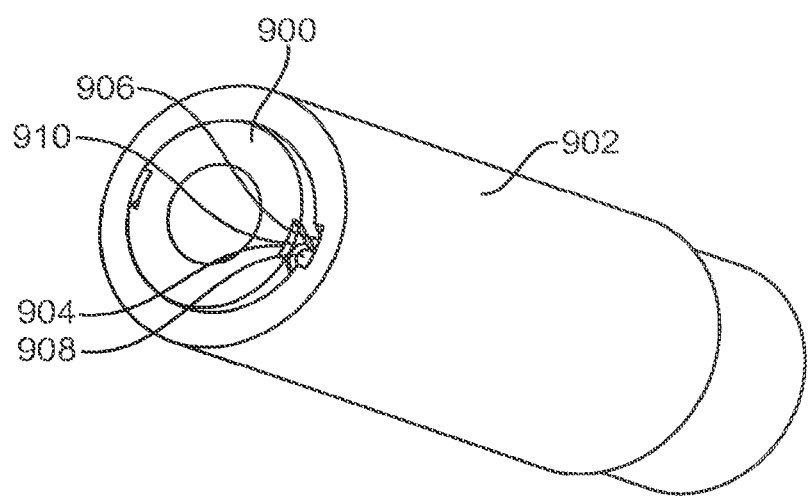
FIG. 30 illustrates a perspective view of an alternative interface between a rotary nut and a housing of an intramedullary rotational correction device like that illustrated in FIGS. 25-27.
Figure 31:
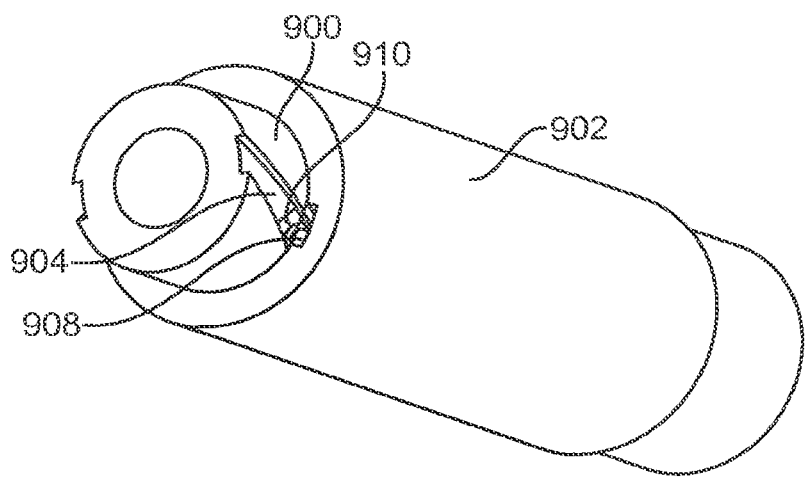
FIG. 31 illustrates a perspective view of the interface after axial and rotational translation of the rotary nut with respect to the housing.
Figure 32:
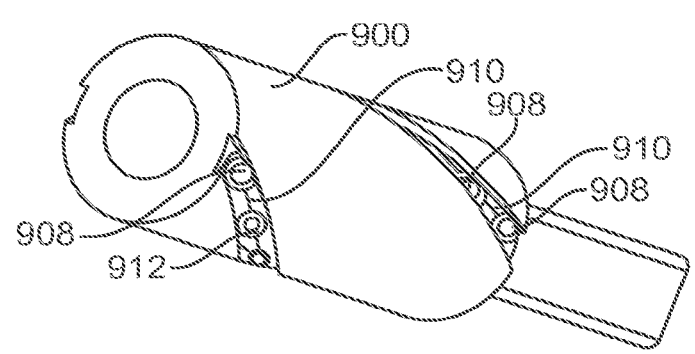
FIG. 32 illustrates a perspective view of the rotary nut with the housing removed for illustration purposes.

FIGS. 30-32 illustrate an alternative embodiment of the interface between a rotary nut 900 and a housing 902 of an intramedullary rotational correction device like that illustrated in FIGS. 25-27. In the embodiment illustrated in FIGS. 26 and 27, non-linear splines 748 located on the rotary nut 744 interface with corresponding grooves 750 disposed along an inner surface of the housing 728. In the alternative embodiment illustrated in FIGS. 30-32, the rotary nut 900 includes one or more non-linear grooves 904 disposed along all or a portion of an exterior surface of the rotary nut 900.

Located opposite the non-linear grooves 904 disposed on the rotary nut 900 are corresponding non-linear grooves 906 disposed along an interior surface of the housing 902. For example, both the non-linear grooves 904 disposed on the rotary nut 900 and the non-linear grooves 906 disposed on the inner surface of the housing 902 may be helical. A plurality of ball bearings 908 are interposed between the non-linear grooves 904 of the rotary nut 900 and the non-linear grooves 906 of the housing 902. As seen in FIG. 32, the plurality of ball bearings 908 may be held stationary by respective cages 910. The cages 910 may include a strip of material substantially aligned with the non-linear grooves 904, 906 and have a plurality of circular pockets 912 that surround and retain individual ball bearings 908. In this manner, the ball bearings 908 are held in a stationary position (for example, in relation to the housing 902) but allowed to spin or rotate within the non-linear grooves 904, 906. For instance, the ends of the cages 910 may be clipped to the ends of the non-linear grooves 906 disposed along the interior surface of the housing 902. In this embodiment, other features of the intramedullary rotational correction device described with respect to FIGS. 25-27 remain the same.

While embodiments of the present invention have been shown and described, various modifications may be made without departing from the scope of the present invention. As one example, the devices described herein may be used to lengthen or reform a number of other bones such as the mandible or the cranium. Thus, while several embodiments have been described herein it should be appreciated that various aspects or elements are interchangeable with other separate embodiments. The invention, therefore, should not be limited, except to the following claims, and their equivalents.

What is claimed is:

1. An intramedullary implant comprising:
   a housing configured to be secured to a first section of bone, the housing including one or more shaft engaging grooves axially extending along an inner surface thereof;
   a distraction shaft configured to be secured to a second section of bone, the distraction shaft including one or more grooves axially extending along an inner surface thereof; and
   an actuator disposed within the housing and operably coupled to the distraction shaft,
   wherein, in response to rotation of the actuator, the one or more grooves of the distraction shaft engage with the one or more shaft engaging grooves of the housing, causing axial displacement of the distraction shaft relative to the housing
   wherein the actuator comprises a rotatable permanent magnet positioned within the housing and a lead screw coupled to the rotatable permanent magnet.

2. The intramedullary implant of claim 1, further comprising one or more ball bearings interposed between the one or more shaft engaging grooves of the housing and the one or more grooves of the distraction shaft.

3. The intramedullary implant of claim 2, wherein the one or more grooves of the distraction shaft include semi-circular indentation configured to allow the one or more ball bearings to roll therein.

4. The intramedullary implant of claim 2, wherein the one or more ball bearings are configured to rotationally lock the one or more grooves of the distraction shaft relative to the one or more shaft engaging grooves of the housing.

5. The intramedullary implant of claim 2, further comprising a plurality of recesses between the one or more shaft engaging grooves of the housing and the one or more grooves of the distraction shaft, the plurality of recesses configured to retain the one or more ball bearings therein.

6. The intramedullary implant of claim 2, wherein each of the one or more ball bearings is sized to engage with a corresponding one of the one or more grooves of the distraction shaft and the one or more shaft engaging grooves of the housing and to prevent rotation between the corresponding one of the one or more grooves of the distraction shaft and the corresponding one of the one or more shaft engaging grooves of the housing.

7. The intramedullary implant of claim 1, further comprising a slip clutch disposed between the rotatable permanent magnet and the lead screw, the slip clutch configured to prevent binding of the rotatable permanent magnet and the lead screw.

8. The intramedullary implant of claim 1, further comprising a sliding seal between the distraction shaft and the housing for providing protection of the implant from an external environment the implant is exposed to.

9. The intramedullary implant of claim 8, wherein the sliding seal includes a plurality of protrusions configured to slidingly seal against the one or more grooves of the distraction shaft.

10. The intramedullary implant of claim 1, wherein the implant is configured to aid in treatment of a limb length discrepancy or a bone defect in the patient's body.

11. An intramedullary implant comprising:
    a housing configured to be secured to a first section of bone, the housing including one or more shaft engaging grooves axially extending along an inner surface thereof;
    a distraction shaft configured to be secured to a second section of bone, the distraction shaft including one or more grooves axially extending along an inner surface thereof; and
    one or more ball bearings interposed between the one or more shaft engaging grooves of the housing and the one or more grooves of the distraction shaft, wherein the one or more ball bearings are configured to rotationally lock the one or more grooves of the distraction shaft relative to the one or more shaft engaging grooves of the housing.

12. The intramedullary implant of claim 11, wherein in response to rotation of an actuator disposed within the housing, the one or more grooves of the distraction shaft engage with the one or more shaft engaging grooves of the housing, causing axial displacement of the distraction shaft relative to the housing.

13. The intramedullary implant of claim 12, wherein the actuator comprises a rotatable permanent magnet positioned within the housing.

14. The intramedullary implant of claim 13, further comprising a lead screw coupled to the rotatable permanent magnet, a slip clutch disposed between the rotatable permanent magnet and the lead screw, the slip clutch configured to prevent binding of the rotatable permanent magnet and the lead screw.

15. The intramedullary implant of claim 11, further comprising a plurality of recesses between the one or more shaft engaging grooves of the housing and the one or more grooves of the distraction shaft, the plurality of recesses configured to retain the one or more ball bearings therein.

16. The intramedullary implant of claim 11, wherein each of the one or more ball bearings is sized to engage with a corresponding one of the one or more grooves of the distraction shaft and the one or more shaft engaging grooves of the housing and to prevent rotation between the corresponding one of the one or more grooves of the distraction shaft and the corresponding one of the one or more shaft engaging grooves of the housing.

17. The intramedullary implant of claim 11, further comprising a sliding seal between the distraction shaft and the housing, the sliding seal includes a plurality of protrusions configured to slidingly seal against the one or more grooves of the distraction shaft.

18. A method of adjusting the first section of the bone with the intramedullary implant of claim 1.

* * * * *